US009586064B2

(12) United States Patent
McHale et al.

(10) Patent No.: US 9,586,064 B2
(45) Date of Patent: *Mar. 7, 2017

(54) ENAMEL PROTECTANT AND REPAIR BRUSHING GELS

(71) Applicant: Premier Dental Products Company, Plymouth Meeting, PA (US)

(72) Inventors: William A. McHale, Collegeville, PA (US); Dale G. Brown, Wharton, TX (US)

(73) Assignee: Premier Dental Products Company, Plymouth Meeting, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/251,149

(22) Filed: Apr. 11, 2014

(65) Prior Publication Data

US 2014/0301957 A1    Oct. 9, 2014

Related U.S. Application Data

(63) Continuation-in-part of application No. 13/651,044, filed on Oct. 12, 2012.

(51) Int. Cl.
*A61Q 11/00* (2006.01)
*A61K 8/23* (2006.01)
(Continued)

(52) U.S. Cl.
CPC ............... *A61Q 11/00* (2013.01); *A61K 8/21* (2013.01); *A61K 8/23* (2013.01); *A61K 8/362* (2013.01);
(Continued)

(58) Field of Classification Search
CPC .......... A61Q 11/00; A61K 8/23; A61K 8/362; A61K 8/891; A61K 8/90; A61K 8/21; A61K 2800/31
See application file for complete search history.

(56) References Cited

U.S. PATENT DOCUMENTS 3,442,842 A    5/1969   Bonin
4,296,096 A *  10/1981  Pierce .................... A61Q 11/00
                                                          424/49
(Continued)

FOREIGN PATENT DOCUMENTS

CN    1093058 A    10/1994
CN    1190342 A    8/1998
(Continued)

OTHER PUBLICATIONS

International Search Report issued in International Application No. PCT/US2013/064504 on Apr. 21, 2014.
(Continued)

*Primary Examiner* — Trevor Love
(74) *Attorney, Agent, or Firm* — Cozen O'Connor

(57) ABSTRACT

Substantially aqueous-free, enamel protectant and repair brushing gels containing: stannous fluoride, calcium and a substantivity agent comprising: an emulsion of polydimethylsiloxane in a nonionic surfactant, wherein substantivity of said stannous fluoride and calcium into biofilm present on enamel is enhanced through calcium binding shifting from bidentate to monodentate in the presence of stannous fluoride; and said brushing gels have substantially improved, enamel protectant factor (EPF) and enamel repair factor (ERF) values compared to fluoride brushing treatments with comparable or higher fluoride levels.

18 Claims, 6 Drawing Sheets

Fluoride Levels, in ppm

(51) Int. Cl.
    *A61K 8/362*     (2006.01)
    *A61K 8/891*     (2006.01)
    *A61K 8/90*     (2006.01)
    *A61K 8/21*     (2006.01)

(52) U.S. Cl.
    CPC ............... *A61K 8/891* (2013.01); *A61K 8/90* (2013.01); *A61K 2800/31* (2013.01)

(56) References Cited

U.S. PATENT DOCUMENTS

| | | |
|---|---|---|
| 4,647,451 A | 3/1987 | Piechota |
| 4,652,441 A | 3/1987 | Okada et al. |
| 4,711,782 A | 12/1987 | Okada et al. |
| 4,911,927 A | 3/1990 | Hill et al. |
| 4,942,034 A | 7/1990 | Hill et al. |
| 5,009,881 A | 4/1991 | Hill et al. |
| 5,032,387 A | 7/1991 | Hill et al. |
| 5,037,639 A | 8/1991 | Tung |
| 5,057,306 A | 10/1991 | Hill et al. |
| 5,057,307 A | 10/1991 | Hill et al. |
| 5,057,309 A | 10/1991 | Hill et al. |
| 5,098,711 A | 3/1992 | Hill et al. |
| 5,165,913 A | 11/1992 | Hill et al. |
| 5,268,167 A | 12/1993 | Tung |
| 5,427,768 A | 6/1995 | Tung |
| 5,437,857 A | 8/1995 | Tung |
| 5,460,803 A | 10/1995 | Tung |
| 5,538,667 A | 7/1996 | Hill et al. |
| 5,562,895 A | 10/1996 | Tung |
| 5,651,959 A | 7/1997 | Hill et al. |
| 5,665,374 A | 9/1997 | Hill et al. |
| 5,665,382 A | 9/1997 | Grinstaff et al. |
| 5,711,935 A | 1/1998 | Hill et al. |
| 5,925,595 A | 7/1999 | Seitz et al. |
| 5,952,317 A | 9/1999 | Deluca et al. |
| 6,054,119 A | 4/2000 | Hurme et al. |
| 6,086,373 A | 7/2000 | Schiff et al. |
| 6,159,449 A | 12/2000 | Winston et al. |
| 6,184,255 B1 | 2/2001 | Mae et al. |
| 6,441,050 B1 | 8/2002 | Chopra |
| 6,534,091 B1 | 3/2003 | Garces Garces et al. |
| 6,545,077 B2 | 4/2003 | Hill et al. |
| 6,569,408 B1 | 5/2003 | Yue et al. |
| 6,575,176 B1 | 6/2003 | Hill et al. |
| 6,740,338 B1 | 5/2004 | Chopra |
| 7,017,591 B2 | 3/2006 | Brown et al. |
| 7,025,986 B2 | 4/2006 | Brown et al. |
| 7,152,611 B2 | 12/2006 | Brown et al. |
| 7,303,921 B2 | 12/2007 | Littarru et al. |
| 7,897,169 B2 | 3/2011 | Ueda et al. |
| 2002/0090398 A1 | 7/2002 | Dunn et al. |
| 2003/0165442 A1 | 9/2003 | Baig et al. |
| 2003/0198604 A1 | 10/2003 | Lawlor |
| 2004/0057908 A1* | 3/2004 | Bowen ................... A61K 8/342 424/49 |
| 2004/0126335 A1 | 7/2004 | Faller et al. |
| 2004/0258634 A1 | 12/2004 | Cazor et al. |
| 2005/0196440 A1 | 9/2005 | Masters et al. |
| 2006/0093558 A1 | 5/2006 | Lin et al. |
| 2006/0120980 A1 | 6/2006 | Eberl |
| 2006/0177384 A1 | 8/2006 | Brown |
| 2006/0286046 A1 | 12/2006 | Haber |
| 2008/0039434 A1 | 2/2008 | Colli |
| 2008/0044454 A1 | 2/2008 | Yang et al. |
| 2008/0050408 A1 | 2/2008 | Hayman et al. |
| 2008/0069781 A1 | 3/2008 | Neuberger |
| 2008/0095719 A1 | 4/2008 | Herrmann et al. |
| 2008/0152598 A1 | 6/2008 | Basic |
| 2008/0152599 A1 | 6/2008 | Brignoli et al. |
| 2008/0175918 A1 | 7/2008 | Laulicht |
| 2008/0226710 A1 | 9/2008 | Fantuzzi |
| 2008/0247973 A1 | 10/2008 | Baig et al. |
| 2008/0286214 A1* | 11/2008 | Brown ................... A61K 8/03 424/52 |
| 2008/0295960 A1 | 12/2008 | Schalau, II et al. |
| 2009/0042161 A1 | 2/2009 | Jodaikin et al. |
| 2009/0087501 A1 | 4/2009 | Cummins |
| 2009/0188520 A1 | 7/2009 | Brown |
| 2009/0232752 A1 | 9/2009 | Carson et al. |
| 2009/0280078 A1 | 11/2009 | Belfer |
| 2010/0135918 A1 | 6/2010 | Kim et al. |
| 2010/0330003 A1 | 12/2010 | Robinson et al. |
| 2011/0014136 A1 | 1/2011 | Kohli et al. |
| 2011/0104052 A1 | 5/2011 | Barnett et al. |
| 2011/0118217 A1 | 5/2011 | Gudmundsson et al. |
| 2012/0021031 A1 | 1/2012 | Chopra et al. |
| 2012/0064136 A1 | 3/2012 | Baker et al. |
| 2012/0129135 A1 | 5/2012 | Yang et al. |
| 2012/0171128 A1 | 7/2012 | Ramirez |
| 2012/0207686 A1 | 8/2012 | Fruge et al. |
| 2012/0245080 A1 | 9/2012 | Goolsbee et al. |
| 2013/0344120 A1 | 12/2013 | Scott et al. |

FOREIGN PATENT DOCUMENTS

| | | | |
|---|---|---|---|
| CN | 101056606 A | 10/2007 | |
| EP | 0 559 262 | 4/1996 | |
| WO | 9511746 A1 | 5/1995 | |
| WO | 9639116 A1 | 12/1996 | |
| WO | WO 01/26577 | 4/2001 | |
| WO | 03068173 A1 | 8/2003 | |
| WO | EP 0868903 * | 11/2006 | ............ A61Q 11/00 |
| WO | 2007036802 A2 | 4/2007 | |
| WO | 2007092811 A2 | 8/2007 | |
| WO | 2007099398 A1 | 9/2007 | |
| WO | 2008047882 A1 | 4/2008 | |
| WO | 2009080022 A1 | 7/2009 | |
| WO | 2010010394 A2 | 1/2010 | |
| WO | WO 2013/039906 | 3/2013 | |
| WO | WO 2014/001132 | 1/2014 | |

OTHER PUBLICATIONS

Wu, L.C., et al., "Anti-inflammatory effect of spilanthol from Spilanthes acmella on murine macrophage by down-regulating LPS-induced inflammatory mediators", J. Agric. Food Chem., vol. 56, No. 7, pp. 2341-2349, Apr. 9, 2008 (Sep. 4, 2008), Abstract.

Attin, T., et al., "Deposition of fluoride on enamel surfaces released from varnishes is limited to vicinity of fluoridation site", Clin Oral Investig, vol. 11, pp. 83-88, 2007.

Belran-Aguillar, E.D., et al., "Fluoride varnishes: A review of their clinical use, cariostatic mechanism, efficacy and safety", JADA, vol. 131, pp. 589-594, 2000.

Caslayska, V., et al., "CaF2 in Enamel Biopsies 6 Weeks and 18 Months after Fluoride Treatment", Caries Res, vol. 25, pp. 21-26, 1991.

Chow, L.C., et al., "Apatitic fluoride increase in enamel from a topical treatment involving intermediate CaHPO4.2H20 formation, an in vivo study", Caries Res, vol. 15, pp. 369-376, 1981.

Christoffersen, J., et al., "Kinetics of dissolution and growth of calcium fluoride and effects of phosphate", Acta Odontol Scand, vol. 46, No. 6, pp. 325-336, 1988.

Crall, J.J., et al., "Enamel fluoride retention after DCPD and APF application and prolonged exposure to fluoride in vitro", J Dent Res, vol. 65, No. 3, pp. 387-389, Mar. 1986.

Cruz, R., et al., "Uptake of KOH-soluble and KOH-insoluble fluoride in sound human enamel after topical application of a fluoride varnish (Duraphat) or a neutral 2% NaF solution in vitro", Scand J Dent Res., vol. 100, No. 3, pp. 154-158, 1992.

Dijkman, A.G., et al., "In vivo investigation on the fluoride content in and on human enamel after topical applications", Caries Res, vol. 17, pp. 392-402, 1983.

Dudev, T., et al., "Monodentate versus bidentate carboxylate binding in magnesium and calcium proteins: what are the basic principles?", J. Phys. Chem. B., vol. 108, pp. 4546-4557, 2004.

Featherstone, J.D.B., "Prevention and reversal of dental caries: role of low level fluoride", Community Dent Oral Epidemiol, vol. 27, pp. 31-40, 1999.

(56) References Cited

OTHER PUBLICATIONS

Featherstone, J.D.B., "The Science and Practice of Caries Prevention", Journal of the American Dental Association, vol. 131, pp. 887-899, 2000.
Helfenstein, U., et al., "Fluoride varnishes (Duraphat): A meta-analysis", Community Dent Oral Epidemiol, vol. 22, pp. 1-5, 1994.
Hong, Y.C., et al., "Enhanced fluoride uptake from mouthrinses", J Dent Res, vol. 64, pp. 82-84, 1985.
Koch, G., "Effect of 250 and 1000 ppm fluoride dentifrice on caries; a three-year clinical study", Swed Dent J, vol. 6, pp. 233-238, 1982.
Margolis, H.C., et al., "Physicochemical perspectives on the cariostatic mechanisms of systemic and topical fluorides", J Dent Res, vol. 69 (Special Issue), pp. 606-613, 1990.
Marinho, V.C., et al., "Fluoride varnishes for preventing dental caries in children and adolescents" (review), Cochrane Database Syst Rev, (3):CD002279, 2002.
Mitropoulos, C.M., et al., "Relative efficacy of dentifrices containing 250 or 1000 ppm F—in preventing dental caries—report of a 32-month clinical trial", Community Dent Health, vol. 1, pp. 193-200, 1984.
Mohammed, N.R., et al., "Effects of Fluoride on in vitro Enamel Demineralization Analyzed by 19F MAS-NMR", Caries Res, vol. 47, pp. 421-428, 2013.
Øgaard, B., et al., "Relative cariostatic effects of KOH-soluble and KOH-insoluble fluoride in situ", J. Dent Res, vol. 69, pp. 1505-1507, 1990.
Øgaard, B., "CaF2 Formation: Cariostatic Properties and Factors of Enhancing the Effect", Caries Res., vol. 35 (Suppl 1), No. 11, pp. 40-44, 2001.
Pendrys, D.G., "Risk of Enamel Fluorosis in Nonfluoridated and Optimally Fluoridated Populations: Considerations for the Dental Professional", Journal of the American Dental Association, vol. 131, No. 6, pp. 746-755, 2000.
Ripa, L.W., "A critique of topical fluoride methods (dentifrices, mouthrinses, operator-, and self-applied gels) in an era of decreased caries and increased fluorosis prevalence", J Public Health Dent., Winter, vol. 51, No. 1, pp. 23-41, 1991.
Rolla, G., et al., "Concentration of fluoride in plaque a possible mechanism", Scand. J. Dent. Res., vol. 85, pp. 149-151, 1977.
Rose, R.K., et al., "A quantitative study of calcium binding and aggregation in selected oral bacteria", J Dent Res, vol. 72, pp. 78-84, 1993.
Schaeken, M.J., et al., "Effects of fluoride and chlorhexidine on the microflora of dental root surfaces and the progression of root-surface caries", J Dent Res, vol. 70, No. 2, pp. 150-153, 1991.
Schemehorn, B.R., et al., "Comparison of Fluoride Uptake into Tooth Enamel from Two Fluoride Varnishes Containing Different Calcium Phosphate Sources", ACP Technology, The Journal of Clinical Dentistry, vol. XXII, No. 2, pp. 51-54.
Schreiber, C.T., et al., "Effects of rinses with an acidic calcium phosphate solution on fluoride uptake, caries and in situ plaque pH in rats", J Dent Res, vol. 67, pp. 959-963, 1988.
Stookey, G.K., "Critical evaluation of the composition and use of topical fluorides", J Dent Res, vol. 69 (Spec Iss), pp. 805-812, 1990.
Tan, H.P., et al., "A randomized trial on root caries prevention in elders", J Dent Res, vol. 89, No. 10, pp. 1086-1090, 2010.
Ten Cate, J.M., "Review on Fluoride with special emphasis on calcium fluoride mechanisms in caries prevention", Eur. J. Oral Sci., vol. 105 (5 pt 2), pp. 461-465, Oct. 1997.
Tewari, A., et al., "Comparative evaluation of the role of NaF, APF, and Duraphat topical fluoride applications in the prevention of dental caries: a 2 1/2 year study", J Indian Soc Pedod Prev Dent, vol. 8, pp. 28-36, 1990.
Tung, M.S., et al., "Dental applications of amorphous calcium phosphates", J. Clin Dent, vol. 10, pp. 1-6, 1999.
Turner, D., et al., "The Interaction of Stannous Fluoride with Synthetic Hydroxyapatite: Modeling the Anticaries Effect", Ceramics—Silikaty, vol. 57, No. 1, pp. 1-6, 2013.
Vaikuntam, J., "Fluoride varnishes: should we be using them?", Pediatr Dent, vol. 22, pp. 513-516, 2000.
Vogel, G.L., et. al., "Salivary fluoride from fluoride dentifrices or rinses after use of a calcium pre-rinse or calcium dentifrice", Caries Res., vol. 40, pp. 449-454, 2006.
Vogel, G.L., et. al., "Calcium Pre-Rinse Greatly Increases Overnight Salivary Fluoride after a 228 ppm Fluoride Rinse", Caries Res., vol. 42, No. 5, pp. 401-404, Sep. 2008.
Vogel, G.L., et. al., "Ca Pre-Rinse Greatly Increases Plaque and Plaque Fluid F", J. Dent. Res., vol. 87, No. 5, pp. 466-469, May 2008.
Vogel, G.L., et al., in "No Calcium-Fluoride-Like Deposits Detected in Plaque shortly after a Sodium Fluoride Mouthrinse", Caries Res., vol. 44, No. 2, pp. 108-115, 2010.
Walton, J.G., et al., "Textbook of Dental Pharmacology and Therapeutics", Oxford University Press 1994, pp. 149 and 154.
Warren, J.J., et al., "A review of fluoride dentifrice related to dental fluorosis", Pediatr. Dent., vol. 21, No. 4, pp. 265-271, Jul.-Aug. 1999.
Zero, D.T., "Dentifrices, mouthwashes, and remineralization/caries arrestment strategies", BMC Oral Health, vol. 6 (Suppl 1), No. 59, pp. 1-13.
Search Report and Written Opinion dated Jul. 2, 2015 which issued in International Patent Application No. PCT/US15/25375.
Search Report and Written Opinion dated Jul. 10, 2015 which issued International Patent Application No. PCT/US15/25385.
Search Report and Written Opinion dated Jul. 2, 2015 which issued in International Patent Application No. PCT/US15/25391.
Search Report and Written Opinion dated Jul. 2, 2015 which issued in International Patent Application No. PCT/US15/25396.
Barry, R., "The Power of Ubiquinol", The Key to Energy, Vitality, and a Healthy Heart, Chapter 4, Studies and Research: The Health Benefits of Ubiquinol, pp. 21-25, 2010.
Bashutski, J.D., et al., "The Impact of Vitamin D Status on Periodontal Surgery Outcomes ", J. Dent. Res., vol. 90, No. 8, pp. 1007-1012, 2011.
Chantal, J., et al., "The coming of age of 1,25-dihydroxyvitamin D3 analogs as immunomodulatory agents", Trends Mol Med., vol. 8, No. 4, pp. 174-179, 2002.
Charig, A. et al., "CE3 Enamel Mineralization by Calcium-containing Bicarbonate Toothpastes: Assessment by Various Techniques", Compendium, vol. 25, No. 9 (Suppl 1), pp. 15-31, Sep. 2004.
Diamond, G., et al., "Host defense peptides in the oral cavity and the lung: similarities and differences", J. Dent. Res., vol. 87, No. 10, pp. 915-927, 2008.
Dietrich, T., et al., Association between serum concentrations of 25-hydroxyvitamin D and gingival inflammation1'2'3', Am. J. Clin. Nutr., vol. 82, No. 3, pp. 575-580, 2005.
Dimeloe, S., et al., "Regulatory T cells, inflammation and the allergic response—The role of glucocorticoids and Vitamin D", Journal of Steroid Biochemistry & Molecular Biology, vol. 120, Issues 2-3, pp. 86-95, 2010.
Emster, L., et al., "Ubiquinol: an endogenous antioxidant in aerobic organisms", Clin Investig, vol. 71, (8 Suppl), pp. 360-S65, 1993.
Folkers, K., "A critique of 25 years of research which culminated in the successful therapy of periodontal disease with menzyme Q10", J. Dent. Health, vol. 42, pp. 258-263, 1992.
Garcia, M., et al., "One-Year Effects of Vitamin D and Calcium Supplementation on Chronic Periodontitis", Journal of Periodontology, vol. 82, No. 1, pp. 25-32, 2011.
Gombart, A.F., "The vitamin D-antimicrobial peptide pathway and its role in protection against infection", Future Microbiology, vol. 4, No. 9, pp. 1151-1165, 2009.
Hanioka, T., et al., "Therapy with Coenzyme Q10 for Patients with Periodontal Disease: 2. Effect of Coenzyme Q10 on the Immune System", Journal of Dental Health, vol. 43, pp. 667-672, 1993.
Hanioka, T., et al., "Effect of Topical Application of Coenzyme Q10 on Adult Periodontitis", Molec. Aspects of Med., vol. 85 (Supplement), pp. S241-S248, 1994.
Hewison, M., "Review: Vitamin D and the intracrinology of innate immunity", Molecular and Cellular Endocrinology, vol. 321, No. 2, pp. 103-111, 2010.
Holick, M.F., "Vitamin D Deficiency", New England Journal of Medicine, vol. 357, pp. 266-281, 2007.

(56) References Cited

OTHER PUBLICATIONS

Holick, M.F., "Vitamin D Status: Measurement, Interpretation, and Clinical Application", Annals of Epidemiology, vol. 19, No. 2, pp. 73-78, 2009.
International Search Report and Written Opinion dated Oct. 12, 2012 which issued in International Patent Application No. PCT/US2013/064358.
Kamen, D.L., et al., "Vitamin D and molecular actions on the immune system: modulation of innate and autoimmunity", J. Mol. Med., vol. 88, pp. 441-450, 2010.
Lei et al., "In Vitro Degradation of Novel Bioactive Polycaprolactone-20% Tricalcium Phosphate Composite Scaffolds for Bone Engineering", Materials and Science and Engineering, vol. 27, Issue 2, Mar. 2007.
Litkowski et al., "CE4, Intraoral Evaluation of Mineralization of Cosmetic Defects by a Toothpaste Containing Calcium, Fluoride, and Sodium Bicarbonate", Compendium, vol. 25, No. 9, Sep. 2004.
Littarru, G.P., et al "Deficiency of coenzyme Q10 in gingival tissue from patients wit periodontal disease", Proc. Natl. Acad. Science USA, vol. 68, No. 10, pp. 2332-2335, Oct. 1971.
McRee, Jr., J.T., et al., "Therapy with coenzyme Q10 for patients with periodontal disease: 1. Effect of Coenzyme Q10 on Subgingival Microorganisms", Journal of Dental Health, vol. 43, pp. 659-666, 1993.
McMahon, L., et al., "Vitamin D-Mediated Induction of Innate Immunity in Gingival Epithelial Cells", Infection and mmunity, vol. 79, pp. 2250-2256, 2011.
Miley, D.D., et al., "Cross-sectional study of vitamin D and calcium supplementation effects on chronic periodontitis", J. Periodontol., vol. 80, No. 9, pp. 1433-1439, Sep. 2009.
Nakamura, R., et al., "Deficiency of Coenzyme Q in Gingiva of Patients with Dental Disease", Internat. J. Vit. Nutr. Res., vol. 43, pp. 85-92, 1973.
Nizet, V., et al., "Cathelicidins and Innate Defense Against Invasive Bacterial Infection", Scandinavian Journal of Infectious Diseases, vol. 35, No. 9, pp. 670-676, 2003.
Oral Health: Different Ages/Different Stages: Birth to 12 12 Years, Ontario, Mar. 2009, pp. 1-24.
Park, K.S., et al., "The short vitamin D receptor is associated with increased risk for generalized aggressive periodontitis", Journal of Clinical Periodontology, vol. 33, No. 8, pp. 524-528, 2006.
Roveri, N., et al., "Surface Enamel Remineralization: Biomimetic Apatite Nanocrystals and Fluoride Ions Different Effects", Journal of Nanomaterials, vol. 2009, Article ID 746383, 9 pages.
Schmelzer, C., et al., "In vitro effects of the reduced form of coenzyme Q10 on secretion levels of TNF$\alpha$ and chemokines in response to LPS in the human monocytic cell line THP-1," Journal of Clinical Biochemistry and Nutrition, vol. 44, No. 1, pp. 62-66, 2009.
Sun, J., "Vitamin D and mucosal immune function", Current Opinion in Gastroenterology,vol. 26, No. 6, pp. 591-594, Nov. 2010.
Tang, P.H., et al., "HPLC Analysis of Reduced and Oxidized Coenzyme Q10 in Human Plasma", Clinical Chemistry, vol. 47, No. 2, pp. 256-265, 2001.
ten Cate, J.M., "Current Concepts on the Theories of the Mechanism of Action of Fluoride", Academic Centre for Dentistry Amsterdam (ACTA), Department of Cariology, Endodontology Pedodontology, Amsterdam, The Netherlands, ACTA Odontol Scand, vol. 57, pp. 325-329, 1999.
Tung, M.S., et al., "CE2, Amorphous Calcium Phosphates for Tooth Mineralization", Compendium, vol. 25, No. 9 (Suppl 1), pp. 9-13, Sep. 2004.
Vieth, R., et al., "Efficacy and safety of vitamin D3 intake exceeding the lowest observed adverse effect level", Am J Clin Nutr, vol. 73, No. 2, pp. 288-294, Feb. 2001.
Wang, X.L., et al., "Cosupplementation with vitamin E and coenzyme Q10 reduces circulating markers of inflammation in baboons1-3", Am. J. Clin. Nutr., vol. 80, No. 3, pp. 649-655, Sep. 2004.
Wang, C., et al., "Association Between Vitamin D Receptor Gene Polymorphisms and Severe Chronic Periodontitis in a Chinese Population", Journal of Periodontology, vol. 80, No. 4, pp. 603-608, 2009.
Wilkinson, E.G., et al., "Bioenergetics in clinical medicine. II. Adjunctive treatment with coenzyme Q10 in periodontal Iherapy", Res. Com. Chem. ath. Pharm. vol. 12, No. 1, p. 111-123, 1975.
Wilkinson, E.G., et al., "Bioenergetics in clinical medicine. VI. Adjunctive treatment of periodontal disease with coenzyme Q10", Res. Com. Chem. Path. Pharm., vol. 14, No. 4, pp. 715-719, 1976.
Xu, H.H.U., et al., "Strong Nanocomposites with Ca PO4, and F Release for Caries Inhibition", J. Dent Res, vol. 89, No. 1, pp. 19-28, 2010.
Supplementary Search Report dated Jul. 8, 2016 which issued in the corresponding European Patent Application No. 13845090.3.
International Preliminary Report on Patentability dated Oct. 20, 2016, issued in corresponding application No. PCT/2015/025385.

* cited by examiner

ENAMEL PROTECTANT AND REPAIR BRUSHING GELS

CROSS REFERENCE TO RELATED APPLICATIONS

This application is a continuation-in-part of U.S. patent application Ser. No. 13/651,044, which was filed with the U.S. Patent and trademark Office on Oct. 12, 2012, entitled "Improved Remineralizing and Desensitizing Compositions, Treatments and Methods of Manufacture"; which specification, includes Examples, Tables and Drawings, are hereby incorporated by reference, in total into the present application. This application is co-pending with U.S. patent application Ser. No. 14/251,104, filed on Apr. 11, 2014, titled "Methods for Protecting and Repairing Enamel".

FIELD OF THE INVENTION

The present invention is directed to advances in enamel protectant and enamel repair, aqueous-free, stannous fluoride, brushing gels; whereby the protectant and repair ingredients are substantive to enamel surfaces, thereby extending the protecting and repairing processes with improved stannous fluoride effectiveness. Key protectant and repair combinations for the brushing gels of the present invention comprise: stannous fluoride and calcium in aqueous-free, substantivity agents.

BACKGROUND OF THE INVENTION

The use of fluoride in anticaries drug products, marketed in the U.S., is carried out under the guidance of the FDA's Fluoride Monograph, 21 CFR 355.10 (revised Apr. 1, 2012).

TABLE 1

| Concentration and Dosage of Stannous Fluoride in Dentifrice/Rinse/Gel products according to the Federal Register 21 CFR 355.10 | |
|---|---|
| Dentifrices | Dentifrices containing 850 to 1,150 ppm theoretical total fluorine in a gel or paste dosage form. Stannous fluoride 0.351 to 0.474% with an available fluoride ion concentration = 700 ppm for products containing abrasives other than calcium pyrophosphate. Stannous fluoride 0.351 to 0.474% with an available fluoride ion concentration = 290 ppm for products containing the abrasive calcium pyrophosphate. |
| Preventive treatment gel | Stannous fluoride 0.4% in an anhydrous glycerin gel, made from anhydrous glycerin and the addition of suitable thickening agents to adjust viscosity. |
| Treatment rinse | Stannous fluoride concentrate marketed in a stable form and containing adequate directions for mixing with water immediately before using to result in a 0.1% aqueous solution. |

Dentifrices

Fluoride dentifrices have been shown in numerous clinical trials to be effective anticaries agents [Stookey, *J. Dent. Res.* 1990, 69(Special Issue): 805-812] and have been recognized as a major cause of the remarkable decline in caries prevalence in many developed countries. Dentifrices have been widely adopted around the world as the principle means of delivering topical fluoride and obtaining caries preventive benefits.

"Washout" of various enamel protectant and enamel repair ingredients from enamel surfaces by saliva flow, eventually controls the effective residence time of various commercial fluoride, enamel protectant and enamel repair, brushing compositions. To improve enamel protectant and enamel repair effectiveness, commercial, professionally prescribed, fluoride, brushing compositions resort to high levels of fluoride, i.e. 5000 ppm for Rx toothpastes, gels and rinses and to approximately 22,000 ppm fluoride for "in-chair", professionally applied varnishes. In addition, standard OTC, fluoride toothpastes can contain up to 1150 ppm fluoride under the FDA's Fluoride Monograph.

The current market for fluoride brushing products includes: professional and consumer oral care fluoride treatments, both OTC and Rx brushing products; including: toothpastes, gels, pastes and varnishes. As noted above, Rx fluoride toothpastes and Rx fluoride brushing gels are well outside fluoride Monograph levels containing up to 5000 ppm fluoride. Professional oral care, in-chair, fluoride varnishes contain up to about 22,000 ppm fluoride, while OTC fluoride toothpastes can contain up to 1150 ppm total theoretical fluorine, the maximum level provided for by the Monograph.

The American Dental Association (ADA); the Food & Drug Administration (FDA) and oral care professionals including: general practitioners, periodontists, orthodontists, pediatric dentists, etc. as a group; are generally concerned over the trend of increasing fluoride levels. These organizations and oral care professionals generally favor using lower levels of fluoride in various in-chair treatments and various OTC and Rx, oral care, topical, home treatments for patients, provided . . . enamel protection and repair, achieved with lower fluoride levels, are comparable to the results reported for brushing products with higher levels of fluoride. This preference for lower fluoride-brushing products is driven by the concern over toxicity, fluorosis in children, etc., associated with exposure to high fluoride levels, long term.

It is generally accepted, approximately 90% of the fluoride used in OTC and Rx fluoride brushing treatments is expectorated after use. Thus, the window for fluoride treatment of enamel is essentially limited to the time fluoride is being brushed onto the enamel. In contrast, fluoride varnishes containing 22,000 ppm fluoride, applied to the enamel by an oral care professional, are designed to maintain substantive fluoride levels on the enamel after patient expectoration.

Fluoride varnishes are generally applied professionally, at a frequency of about once every six months with the target audience comprising primarily children.

Dietary fluoride levels have gradually increased due to fluoridated drinking water and the fluoride in water used in food preparation, etc. In addition, most consumers use fluoride: toothpastes, rinses, gels, etc. Extensive literature citations indicate topical fluoride treatments are more effective in protecting and repairing enamel than treatment with systemic fluorides.

See: Ripa, *Public Health Dent.*, 1991; 51:23-41.

Yet, with all this fluoride available, caries continues to pose a challenge: in children, as well as adults including coronal caries in the elderly, caries in dry mouth patients, caries in immunocompromised patients, caries in patients undergoing medical or dental treatment, etc.

There is a need to improve enamel protectant and enamel repair effectiveness for professional oral care, fluoride treatments, as well as for OTC fluoride products for patient use, while reducing the risk associated with exposure to high fluoride levels.

Additionally, there is a need to improve the efficacy of fluoride products in the area of enamel protection and enamel repair, where the efficacy of various fluoride treatments is assessed as a function of the fluoride level used to effect treatment of various conditions of the enamel.

OBJECTS OF THE PRESENT INVENTION

To provide fluoride brushing gels with improved enamel protectant factor (EPF) values and improved enamel repair factor (ERF) values.

To provide fluoride brushing gels with improved EPF and ERF values, where improvements in EPF and ERF values can be achieved with reduced fluoride content in the brushing gels.

To reduce fluoride levels in brushing gels, while attaining comparable or improved EPF and ERF values, compared to current, commercial, fluoride brushing products, as well as fluoride brushing products described in the prior art.

To improve EPF and ERF brushing gels for "at-risk" patients.

To provide brushing gels that improve challenged enamel conditions of "at-risk" patients including immunocompromised patients; cancer therapy, cardio treatment, diabetes, COP patients; etc.

DEFINITION OF TERMS

The following terms used throughout this specification and claims to describe features of the brushing gels of the present invention are described below:

"Aqueous-free" is defined as: substantially free from water.

"Enamel Protectant Factor (EPF)" is defined as: the percent reduction in enamel solubility divided by the fluoride level in parts per million using FDA method #40.

"Enamel Repair Factor (ERF)" is defined as: the average increase in enamel fluoride concentration divided by the fluoride level of the fluoride brushing product tested using FDA method #33.

"Brushing gel" is defined as: a non-abrasive fluid for administration of stannous fluoride to enamel surfaces.

"Mucoadhesive" is defined as: a substance that is retained for a period of time onto surfaces in the mouth that is not easily removed by the mechanical action of the tongue nor by flow of saliva.

"Stable stannous fluoride" is defined as: compositions that, when chemically assayed, substantially retains the level of stannous and/or fluoride in an unreacted state.

"Biofilm" is defined as: a surface adherent film comprised of bacteria, exuded polysaccharides, etc., that is not easily removed by mechanical means or saliva flow.

"Substantivity agent" is defined as: a composition that improves the mucosal retention of the desired agents.

"Cation bridging" is defined as: electrical attraction between two films or membranes initiated by cation moieties.

"Shift in calcium binding from bidentate to monodentate" is defined as: the loss of "chelate"-like binding by calcium cations with a corresponding increase in single ligand binding by calcium cations.

"Liquid nonionic surfactant" is defined as: a liquid composition that indicates surface active properties with the absence of charged species.

"Solid nonionic surfactant" is defined as: a solid composition that indicates surface active properties with the absence of charged species.

"$CaF^+$ moiety" is defined as: a monodentate calcium fluoride ion.

"Linear, polymeric, polycarboxylates, substantivity enhancer" is defined as: a linear polymer with carboxylate substituents that increases retention of compositions onto charged surfaces.

"Emulsion discontinuous phase" is defined as: the minor component in an emulsion that is surrounded by a continuous phase.

"Emulsion continuous phase" is defined as: an emulsion component that surrounds discontinuous phase component.

SUMMARY OF THE INVENTION

The present invention is directed to aqueous-free, brushing gel compositions, wherein the brushing gels contain stannous fluoride and calcium in an aqueous-free, substantivity agent. The brushing gels of the present invention protect and repair enamel more effectively than brushing gels and toothpaste compositions containing comparable or substantially higher levels of fluoride, as indicated by comparative EPF and ERF values reported herein.

The unexpected enamel protectant and enamel repair features of the brushing gels of the present invention, as detailed below in the Examples, Tables and Drawings; are attributed to unique, aqueous-free, brushing gel compositions, which feature:
  (a) stannous fluoride and calcium;
  (b) a substantivity agent; and
  (c) cation bridging associated with microbial fluoride binding.

The enamel protectant and enamel repair, brushing gel compositions of the present invention, when brushed onto enamel, form substantive, mucoadhesive gels in the presence of saliva; which mucoadhesive gels gradually release stable stannous fluoride and calcium onto enamel. This slow release continues until the mucoadhesive gel is eventually totally solubilized by saliva. This gradual release minimizes the "wash-out" effect traditionally experienced with fluoride brushing products. The resultant enamel protectant and enamel repair increases in EPF and ERF values, resulting from the extended enamel residence time of stannous fluoride, calcium and cation bridging associated with microbial fluoride binding to biofilm. This improved stannous fluoride efficiency reduces the need to resort to elevated fluoride levels.

Traditionally, fluoride brushing products with strong taste characteristics have been reported to cause excessive salivary stimulation, which increases the rate of fluoride clearance from the mouth. In contrast, the brushing gels of the present invention with exceptionally strong, taste characteristics, including "tingle", mouthfeel and hedonic characteristics that mask the metallic taste of stannous fluoride; surprisingly indicate increased "residence time" and extend the availability of stannous fluoride, thereby effecting enamel fluoride uptake and enamel protection values (ERF and EPF, respectively) superior to commercial, stannous fluoride, brushing products.

BRIEF DESCRIPTION OF THE DRAWINGS

In FIG. 2, the 300 ERF value is for a test gel, stannous fluoride at 970 ppm fluoride; the 170 ERF value is for Crest® PRO-HEALTH®, stannous fluoride at 1100 ppm fluoride; and the 65 ERF value is for Clinpro® 5000, sodium fluoride at 5000 ppm fluoride. In FIG. 3 the 270 ERF value is for a test gel, stannous fluoride at 970 ppm fluoride; and the 140 ERF value is for Crest® PRO-HEALTH®, stannous fluoride at 1100 ppm fluoride.

In FIG. 5 the 410 ERF value is for a test gel, stannous fluoride at 970 ppm fluoride; and the 210 ERF value is for Crest® PRO-HEALTH®, stannous fluoride at 1100 ppm fluoride. In FIG. 6 the ERF value of 1070 is for a test gel, stannous fluoride at 970 ppm fluoride; and the ERF value of 210 is for Crest® PRO-HEALTH®, stannous fluoride at 1100 ppm fluoride.

DETAILED DESCRIPTION OF THE INVENTION

Figure 1:
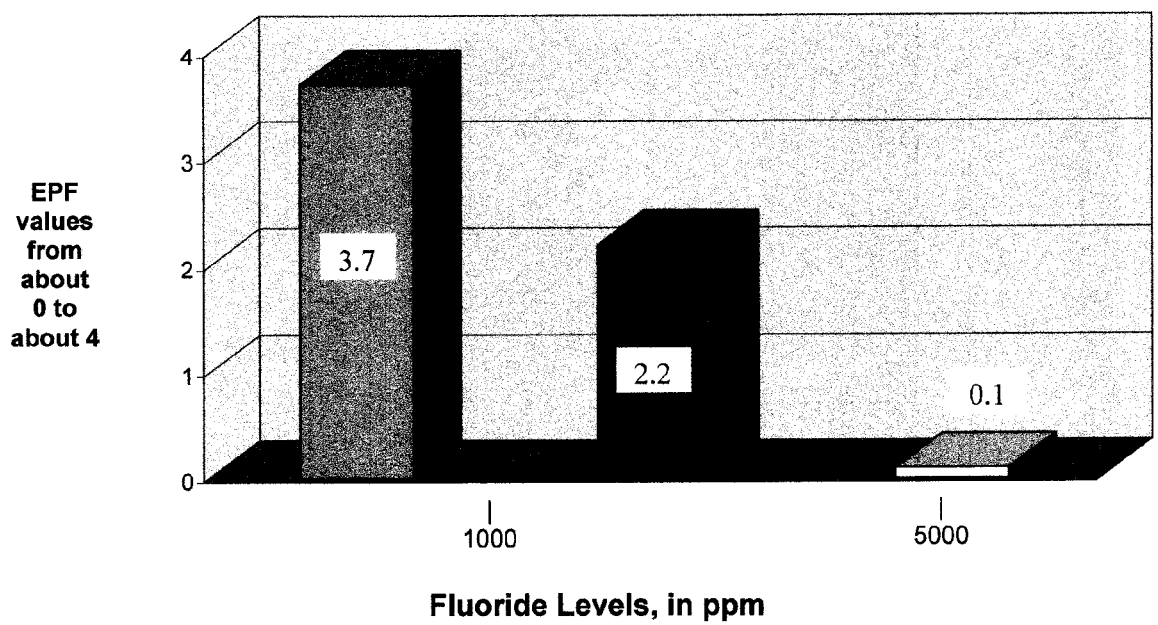
FIG. 1 of the Drawings summarizes comparative, in vitro, enamel protectant factor (EPF) values for enamel treated with a brushing gel of the present invention with stannous fluoride at 970 ppm fluoride, as described in Example 1; compared with: (a) an Rx 5000 ppm, sodium fluoride toothpaste, and (b) an OTC, 1100 ppm, stannous fluoride toothpaste. The 3.7 EPF value is for a test gel, stannous fluoride at 970 ppm fluoride. The 2.2 EPF value is for Crest® PRO-HEALTH®, stannous fluoride at 1100 ppm fluoride. The 0.1 EPF value is for Clinpro® 5000, sodium fluoride at 5000 ppm fluoride.

Aqueous-free, stannous fluoride, calcium, brushing gels of the present invention comprise substantivity agents that contain various enamel protectant and enamel repair ingredients. These substantivity agents function as carriers for various enamel protectant and repair ingredients. These substantivity agents are characterized by their ability, in the presence of saliva, to form mucoadhesive gels which are substantive to enamel with biofilm. These substantive, mucoadhesive gels are further characterized by their ability to: (a) gradually dissolve when exposed to saliva flow, and (b) gradually release various enamel protectant and enamel repair ingredients, in an unreacted state, onto enamel surfaces with biofilm as they dissolve. This gradual dissolution feature of these mucoadhesive gels minimizes saliva "washout" of enamel protectant and enamel repair ingredients by gradually releasing these ingredients onto enamel surfaces with biofilm. The substantivity agents of the present invention extend the duration of enamel protectant and enamel repair treatments, and support cation bridging associated with microbial fluoride binding; thereby enhancing the EPF and ERF values of various brushing gels of the present invention, while simultaneously reducing the level of fluoride required to achieve the unexpected increases in EPF and ERF values.

In as preferred embodiment of the invention, phosphate components are also included in the brushing gels. These are described by Ming Tung in U.S. Pat. Nos. 5,037,639; 5,268,167; 5,427,768; 5,437,857; 5,460,803; 5,562,895; by Tung in the American Dental Association Foundation publication, "ACP Technology,"; by Schemehorn, et. al., in *The Journal of Clinical Dentistry* Vol. XXII: No 2. 51-54, 2011; by the 19 references cited by Schemehorn, et. al.; and by the description of various Gantrez® resins containing calcium, including Gantrez® MS-955 available from International Specialty Products, Wayne, N.J., USA.

The aqueous-free, substantivity agents of the present invention hold the various enamel protectant and enamel repair ingredients, including stannous fluoride, calcium and phosphate components, in a condition where these ingredients remain stable and unreacted. When this aqueous-free, substantivity agent is exposed to saliva, it forms a mucoadhesive gel that is substantive to enamel with biofilm. This mucoadhesive gel continues to hold the enamel protectant and enamel repair ingredients onto enamel surfaces with biofilm without the ingredients reacting. These ingredients eventually react upon being released onto saliva- and biofilm-coated, enamel surfaces.

Eventually, this mucoadhesive, substantivity agent is totally dissolved by saliva, releasing the balance of unreacted enamel protectant and enamel repair ingredients onto saliva- and biofilm-coated, enamel surfaces.

Aqueous-free, brushing gels of the present invention contain enamel protectant and enamel repair ingredients, suitable for protecting and repairing dental enamel; wherein:
(1) said aqueous-free, brushing gels inhibit premature reaction of the enamel protectant and enamel repair ingredients;
(2) the enamel protectant and enamel repair ingredients are released onto enamel with biofilm via saliva that solubilizes substantivity agents that are substantive to: enamel, dentin, biofilm and pellicle;
(3) the enamel protectant and enamel repair ingredients contained in the substantivity agents are gradually released onto the enamel in an unreacted state as the saliva soluble, substantivity agent undergoes saliva dissolution at rates, which are controlled by saliva flow and the composition of the substantivity agent; and
(4) bidentate binding of calcium shifts to monodentate binding of calcium in the presence of stannous fluoride.

For purposes of the present invention, saliva soluble, aqueous-free emulsions used as substantivity agents include those emulsions that are comprised of polydimethylsiloxane polymers in solid nonionic surfactants, as described in U.S. Pat. Nos. 5,032,387; 5,098,711; 5,538,667; 5,651,959; having the structural formula:

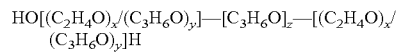

wherein the sum of x, y and z is between 120 and 150. In a preferred embodiment, x=76, y=0 and z=56;

liquid, nonionic surfactants, having the structural formula:

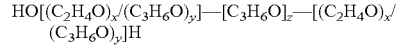

wherein the sum of x, y and z is between 125 and 175. In a preferred embodiment, x=76, y=25 and z=56;

and combinations of solid and liquid, nonionic surfactants, wherein the mixture is liquid. The foregoing references are hereby incorporated herein by reference.

In a preferred embodiment of the invention, liquid, nonionic surfactants comprise the continuous phase of the aqueous-free emulsions. These liquid, nonionic surfactants are selected from the group consisting of: poloxamer, having the structural formula set out above, as well as mixtures of such liquid, nonionic surfactants with solid, nonionic surfactants; wherein the mixture is liquid, including: solid, nonionic surfactants having the structural formula set out above.

Preferred aqueous-free, saliva soluble emulsions for use as substantivity agents of the present invention include aqueous-free emulsions comprising a liquid, nonionic, continuous phase and a discontinuous phase of polydimethylsiloxane (PDMS) at viscosities ranging from between about 1500 cs and about 2.5 million cs. Particularly preferred, aqueous-free emulsions include a liquid, nonionic, surfactant, continuous phase and a discontinuous phase PDMS at viscosities between about 10,000 cs and 2.5 million cs.

Solid surfactants, useful as adjuncts to liquid, nonionic, surfactant, continuous phase are described in detail in U.S. Pat. No. 5,651,959. These liquid and liquid/solid, nonionic, surfactant emulsion mixtures are liquid and form mucoadhesive gels in the presence of saliva.

Preferred polydimethylsiloxanes are selected from the group consisting of polydimethylsiloxane: at 1500 cs, at 10,000 cs, at 100,000 cs, at 250,000 cs, at 500,000 cs, at 750,000 cs, at 1.5 million cs, at 2.2 million cs, at 2.5 million cs and combinations thereof.

Foam modulators are useful in the present invention. These include, without limitation: materials operable to control amount, thickness or stability of foam generated by the brushing gel composition upon agitation. Any orally acceptable foam modulator can be used, including polyethylene glycols (PEGs), also known as polyoxyethylenes. High molecular weight PEGs are suitable, including those having an average molecular weight of about 200,000 to about 7,000,000, for example about 500,000 to about 5,000,000 or about 1,000,000 to about 2,500,000. One or more PEGs are optionally present in a total amount of about 0.1% to about 10%, for example about 0.2% to about 5% or about 0.25% to about 2%.

Humectants useful for the brushing gels of the present invention include, without limitation: polyhydric alcohols such as glycerin, sorbitol, xylitol or low molecular weight PEGs. In various embodiments, humectants can prevent hardening of the brushing gels upon exposure to air. In various embodiments, humectants also function as sweeteners.

Any other desired components may be added to the compositions, including, for example, additional: mouthfeel agents, pH modifying agents, flavorants, sweeteners, antimicrobial (e.g., antibacterial) agents such as those described in U.S. Pat. No. 5,776,435, saliva stimulants, anti-inflammatory agents, nutrients, vitamins, proteins, antioxidants, colorants, etc.

invention contain stannous fluoride at a level of 970 ppm, compared with: (a) a 900 ppm sodium fluoride toothpaste, and (b) an 1100 ppm stannous fluoride toothpaste or (c) a 5000 ppm sodium fluoride toothpaste.

Tables 2 through 10 summarize:

(a) EPF or ERF data for brushing gels of the invention at varying compositions, as described in Examples 1 through 5, compared with commercial, fluoride, brushing products;

(b) Illustrative Examples of brushing gels of the invention; and (c) Illustrative Treatments with brushing gels of the invention.

In a preferred embodiment, the brushing gels of the present invention contain ingredients that substantially effect enamel protection factor (EPF) and enamel repair factor (ERF) values based on bidentate binding of calcium shifting to monodentate binding of calcium in the presence of stannous fluoride. These include:

Stannous fluoride, calcium and phosphate components, and

Substantivity agents and substantivity enhancers including mixed sodium and calcium salt copolymers of methyl/vinyl/ether/maleic acid;

wherein the stannous fluoride, calcium and phosphate components remain unreacted and the pH of the brushing gel when administered to saliva coated enamel is at least about 3.

The foregoing ingredients are described in detail below.

Stannous Fluoride Concentration

The amount of stannous fluoride in the brushing gels of the present invention, applied to the toothbrush (dose) is not as important as the concentration of available stannous fluoride in the brushing gel. Heretofore, reducing fluoride concentration in brushing products has been reported not to be as effective as regular concentration fluoride products.

Petersson, et. al., *Swed. Dent.* 1982, 6:233-238

Metropoulos, et. al., *Community Dent. Health*, 2002, 1:193-200.

The extraordinary EPF and ERF values of the brushing gels of the present invention allow for reducing stannous fluoride concentrations while effecting acceptable fluoride protection and uptake results.

The fluoride dose is important in regard to enamel fluorosis in children under six years of age, due to fluoride brushing gel ingestion. For this reason, reducing the amount of stannous fluoride applied with the brushing gel of the present invention is a preferred strategy over lowering the dose of stannous fluoride brushing gels of the invention intended for use by children under six years of age.

While fluoride brushing products have a long history of safety, there is a continuing concern associated with dental fluorosis due to fluoride ingestion in children under age six. Dendrys, *J. Am. Dent. Assoc.* 2000, 131(6): 746-755.

Studies have shown that for children 1-3 years of age, 30 to 75% of the fluoride brushing product is ingested; and for children 4-6 years of age, 14 to 48% is ingested. Warren and Levy, *Pediatr. Dent.*, 199, 21:265-271.

Stannous fluoride brushing gels of the present invention, with their improved efficacy can be used at reduced stannous fluoride levels, and thereby substantially lower the risk of overdosing and the onset of fluorosis, while delivering effective EPF and ERF results.

See also Zero, *BMC Oral Health*, 2006, 6(Suppl 1): 59; 1-13.

Monitoring the Fluoride-Mineral Phase Formed on Enamel as a Function of the Concentration of Fluoride Ions [$F^-$] in the Demineralizing Medium See: Mohammed, et. al., *Caries Res.*, 2013; 47:421-428.

At below 45 ppm [$F^-$] in the solution $^{19}F$ MAS-NMR showed fluoride-substituted apatite formation, 1B $^{19}F$ magic angle, spinning nuclear magnetic resonance was used to characterize the solid phase precipitated on enamel as a function of fluoride concentration during exposure of the enamel to an in vitro demineralization system. The cariostatic effect of fluoride is due to the formation of $F_s$a HAP and $CaF_2$ depending on the [$F^-$] level in the solution.

Above 45 ppm, calcium fluoride ($CaF_2$) is formed in increasing proportions

Further increases in [$F^-$] caused no further reduction in demineralization, but increased the proportion of $CaF_2$ formed.

As to the mechanism of fluoride anticaries efficacy . . . fluoroapatite formation in enamel is investigated.

Advantages of $^{19}$F MAS-NMR:
(1) selectively probes the local environment of only fluorine atoms in the sample, permitting direct identification of the possible structural forms in which [F$^-$] may exist within the enamel.
(2) detects all fluorine present, whether:
   crystalline,
   amorphous, or
   adsorbed.
(3) measures very low concentration of fluoride in the order of 0.1%.

$^{19}$F MAS-NMR established the effects of varying fluoride concentrations on fluoride-enamel interactions under acidic conditions using bulk enamel blocks rather than powder.

For the samples demineralized in the presence of [F$^-$]:
(1) chemical shifts were identified;
(2) formulation of fluoride-substituted apatite: [a] $(Ca_{10}CPO_4)_6F_{2-x}$, ($F_s$-HAP); and
(3) formation of CaF2;
   were observed in approximately aged proportion at 45 ppm [F$^-$] solutions.
   At [F$^-$] above 45 ppm less $F_s$-HAP forms and an increased signal for CaF
   For [F$^-$] above 136 ppm mostly $CaF_2$ was identified.

The present study demonstrates that the addition of fluoride produces Fs-HAP as a major chemical species only at low concentrations of fluoride.

There is overwhelming evidence that low fluoride levels found in:
(a) saliva can significantly reduce enamel demineralization, and
(b) plaque has the potential to remineralize even at pH values typically regarded as demineralizing.

Calcium, $CaF_2$, $CaF^+$ and Phosphate

Tin:
The ability of the tin ions to inhibit plaque formation has been studied primarily using stannous fluoride mouthrinses. Daily rinsing with a 0.1 percent stannous fluoride solution significantly reduces bacterial accumulation on the teeth.

The action of stannous ions is mediated through their ability to bind to lipotechoic acid on the surface of Gram-positive bacterial. The surface net charge of the organisms is therefore reversed and the adsorption of the cells onto teeth is consequently reduced. Furthermore, the effectiveness of stannous fluoride solution in reducing bacterial adhesion is related to the stability of the stannous ions in aqueous solution and the rate at which they are taken up and retained by specific bacteria. The accumulation of tin in bacteria may alter their metabolism and other physiochemical characteristics.

Stannous Fluoride:
This also reduces dentine sensitivity. In solution it undergoes spontaneous hydrolysis and oxidation, so it is applied in the form of a gel mixed with carboxymethylcellulose or glycerin. Stannous fluoride acts as an enzyme poison and may inactivate enzymic activity in the odontoblastic process. Like sodium fluoride, stannous fluoride induces mineralization within the dentinal tubules, which creates a calcific barrier in the dentine surface.

Christofferson, et. al., in *ACTA ODONTOL. SCAND.* 1988, 46:325-336, reports:
"It is suggested that the calcium fluoride-like material formed on dental enamel during treatment of enamel with acidified solutions of high fluoride content is a phosphate-containing calcium fluoride."

"The aims of the present work are to determine the rates of growth and dissolution of pure calcium fluoride in aqueous suspensions and possible mechanisms controlling these processes, and to study the properties of the calcium fluoride-like material formed by adding fluoride to systems containing hydroxyapatite crystals and/or dissolved calcium and phosphate, simulating the type of calcium fluoride-like material formed on dental enamel as a result of topical treatment with acidified solutions of high fluoride content."

"From our results of dissolution of pure $CaF_2$ in systems containing phosphate it can be seen that 1 µm phosphate has a dramatic effect on the rate of dissolution of $CaF_2$."

"The calcium fluoride-like materials containing phosphate appear to be more likely candidates to serve as slow fluoride release agents."

B. Øgaard's "$CaF_2$ Formation: Cariostatic Properties and Factors of Enhancing the Effect," *Caries Res.*, 2001; 35 (Suppl) 11:40-41, teaches:

"$CaF_2$ or a $CaF_2$-like material/phosphate-contaminated $CaF_2$ is a major reaction product during topical treatment of dental hard tissues. Recently, evidence has suggested that $CaF_2$ is formed not only on surfaces but also to some extent in the enamel. The minimum concentration of fluoride required for $CaF_2$ formation is not well known and may depend on whether calcium is available from plaque fluid or only through dissolution of the dental hard tissue. Furthermore surface adsorption of fluoride to crystals may cause local concentrations necessary for $CaF_2$ formation. It has been suggested that $CaF_2$ acts as a pH-controlled reservoir of fluoride. The rate-controlling factor appears to be phosphate, which controls the dissolution rate of $CaF_2$ at high pH. Increasing fluoride concentration, prolonging the exposure time or using a fluoride solution with low pH can increase $CaF_2$ formation. $CaF_2$ formed at low pH contains less internal phosphate which has been shown to be less soluble. This may be of clinical significance for fluoride applied topically a few times per year."

"The interaction between the fluoride ion and dental hard tissues has been investigated extensively since modern fluoride research started in the 1940s. The chemistry of this process is complicated due to many impurities in hydroxyapatite-like carbonate and magnesium and to a large variety of fluoride concentrations, pH and composition of the agents used in caries prevention. During pH cycling in plaque, fluoride may exchange with hydroxyl in the apatite and a series of solids with intermediate composition and crystallographic properties are formed known as fluorhydroxyapatite."

"$CaF_2$ is the major or probably the only reaction product on dental hard tissues from short treatments with relatively concentrated fluoride agents (Cruz et. al., *Scand. J. Dent. Res.*, 1992; 100:154-158). Without doubt, this pH-controlled depot of $CaF_2$ plays a major role in the cariostatic effect of topical fluoride. $CaF_2$ has been detected on dental hard tissues weeks and months after a single topical fluoride treatment (*Caries Res.*, 1991, 25:21-26) and is the only logical way to explain that such treatments have a cariostatic effect. By treating enamel samples subjected to topical fluoride treatment with KOH, the cariostatic effect is lost (Øgaard, et al., *J. Dent. Res.*, 1990, 69:1505-1507)."

J. M. ten Cate's "Review on Fluoride, with special emphasis on calcium fluoride mechanisms in caries prevention", Eur. J. Oral Sci., 1997, 105:461-465, teaches:

"For treatments to be effective over periods longer than the brushing and the following salivary clearance, fluoride needs to be deposited and slowly released. Calcium fluoride (or like) deposits act in such a way, owing to a surface covering of phosphate and/or proteins, which makes the $CaF_2$ less soluble under in vivo conditions than in a pure form in inorganic solutions. Moreover, due to the phosphate groups on the surface of the calcium fluoride globules, fluoride is assumed to be released with decreasing pH when the phosphate groups are protonated in the dental plaque."

"In the presence of low concentrations of fluoride in solution (such as saliva or plaque fluid), hydroxyapatite might be dissolved below the critical pH (for hydroxyapatite), but the released mineral ions could be reprecipitated as fluoroapatite or a mixed fluor-hydroxyapatite. This mechanism prevents the loss of mineral ions, while providing additional protection to mineral crystallites by laying fluoride-rich other layers onto the apatite crystallites."

"These observations point to the presence of slowly releasing fluoride reservoirs, either on the dentition or the mucosal surfaces. Recent work has shown that in particular the oral mucosa, both by its chemical and morphological nature and the large surface area, is an underestimated retention site of fluoride."

"Research has shown that small amounts of fluoride in plaque and saliva are sufficient to shift the de, remineralization balance favorably. Such levels should then be available throughout the day, in particular during periods of carbohydrate fermentation in the plaque. A fluoride-releasing reservoir system, effective at low pH, such as shown for calcium fluoride, would be a preferred system."

Vogel, et al., in "No Calcium-Fluoride-Like Deposits Detected in Plaque shortly after a Sodium Fluoride Mouthrinse", Caries Res., 2010; 44:108-115, reported:

"Plaque 'calcium-fluoride-like' (CaF2-like) and fluoride deposits held by biological/bacterial calcium fluoride (Ca—F) bonds appear to be the source of cariostatic concentration of fluoride in plaque fluid. The aim of this study was to quantify the amounts of plaque fluoride held in these reservoirs after a sodium fluoride rinse."

"The results suggest that either CaF2-like deposits were not formed in plaque or, if these deposits had been formed, they were rapidly lost. The inability to form persistent amounts of $CaF_2$-like deposits in plaque may account for the relatively rapid loss of plaque fluid fluoride after the use of conventional fluoride dentifrices or rinses."

"Based on laboratory [Margolis and Moreno, J. Dent. Res., 1990, 69 (Spec. Issue) 606-613; J. Am. Dent. Assoc., 2000, 13:887-889; and clinical observations (reviewed by Featherstone, J. American Dent. Assoc., 2000, 13:887-889; the current models for increasing the anticaries effects of fluoride (F) agents emphasize the importance of maintaining a cariostatic concentration of F in oral fluids."

"This inability to form potentially more persistent calcium fluoride deposits, which appears to be due to the low concentration of oral fluid Ca, may account for the relatively rapid loss of F in plaque after the use of current over-the-counter topical F agents. It should be noted in this regard that (1) studies in which a Ca preapplication was used to ameliorate this situation have produced very large and persistent increases in both plaque fluid and that salivary fluoride (Vogel, et. al., Caries Res., 2006, 40:449-454; Vogel, et. al., Caries Res. 2008 (a) 421; 401-404; and Vogel, et. al., J. Dent. Res. 2008(b) 87:466-469; and that (2) preliminary studies (unpubl.) using modifications of the techniques described here confirm that the use of a Ca prerinse prior to a F rinse indeed forms large amounts of $CaF_2$-like deposits."

Substantivity Agents

For purposes of the present invention, substantivity agent refers to a composition or combination of compositions that, when administered to oral cavity surfaces with biofilm, enhance the retention of stannous fluoride and calcium to said oral cavity surfaces.

The unexpected enamel protectant and enamel repair features of the aqueous-free, brushing gels of the present invention are attributed to the unique substantivity properties indicated by the brushing gels of the invention.

For purposes of the present invention, preferred substantivity agents for the brushing gels of the present invention include various aqueous-free emulsions of polydimethylsiloxane/polymers in nonionic surfactants at viscosities of at least about 10,000 cs.

These substantivity agents form mucoadhesive gels in the presence of saliva, which are substantive to biofilm-coated enamel and gradually dissolve under saliva flow, releasing stannous fluoride onto the biofilm on the enamel at a pH of at least about 3; thereby effecting EP F and ERF values of at least about 2.5 and about 200, respectively.

For purposes of the present invention, substantivity agents include saliva soluble, aqueous-free emulsions comprised of:

polydimethylsiloxane polymers in solid, nonionic surfactants, as described in U.S. Pat. Nos. 5,032,387; 5,098,711; 5,538,667; 5,645,841; 5,651,959; having the following structural formula:

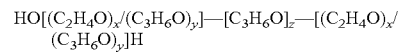

wherein y=0 and the sum of x and z is between 120 and 150. In a preferred embodiment, x=76, y=0 and z=56;

and liquid nonionic surfactants having the following structural formula:

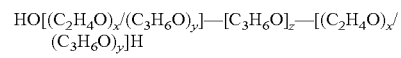

wherein the sum of x, y and z is between 125 and 175. In a preferred embodiment, x=76, y=25 and z=56.

Combinations of solid and liquid, nonionic surfactants are also suitable for purposes of the present invention, provided the resultant emulsion remains liquid. All of the foregoing references are hereby incorporated herein by reference.

In a preferred embodiment of the invention, liquid nonionic surfactants comprise the continuous phase of the aqueous-free emulsions. Preferred liquid nonionic surfactants are represented by the structural formula:

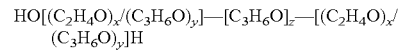

wherein x=76, v=26 and z=56.

Combinations of liquid, nonionic surfactants with solid, nonionic surfactants are also preferred, including solid nonionic surfactants having the structural formula:

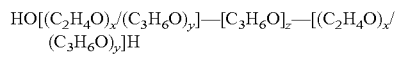

wherein x=76, y=0 and z=56, are suitable.

Preferred aqueous-free, saliva soluble emulsions for use in the substantivity agents of the present invention include aqueous-free emulsions comprising a liquid, nonionic, continuous phase and a discontinuous phase of polydimethylsiloxane (PDMS) at viscosities ranging from between about 1500 cs and about 2.5 million cs. Particularly preferred are aqueous-free emulsions with a liquid, nonionic surfactant continuous phase and a discontinuous PDMS phase at viscosities between 10,000 cs and 2.5 million cs. Solid surfactants, useful as adjuncts to the liquid nonionic surfactant continuous phase are described in detail in U.S. Pat. No. 5,651,959. These liquid and liquid/solid nonionic surfactant emulsions form mucoadhesive gels in the presence of saliva.

Preferred polydimethylsiloxanes are selected from the group consisting of polydimethylsiloxane: at 1500 cs, at 10,000 cs, at 100,000 cs, at 250,000 cs, at 500,000 cs, at 750,000 cs, at 1.5 million cs, at 2.2 million cs, at 2.5 million cs and combinations thereof.

In a preferred embodiment of the invention, copolymers described below are useful as substantivity enhancers; when combined with the aqueous-free, substantivity agents of the present invention. These substantivity enhancers include various linear polymeric, polycarboxylates, such as: copolymers of sodium and calcium salts of methyl/vinyl/ether/maleic acid including those copolymers available commercially as Gantrez® MS-955 polymer, a mixed sodium and calcium salt of methyl/vinyl/ether/maleic acid copolymer; where the cations form salt bridges which cross-link the polymer chains.

The chemical structure of this copolymer is represented by the following chemical structure:

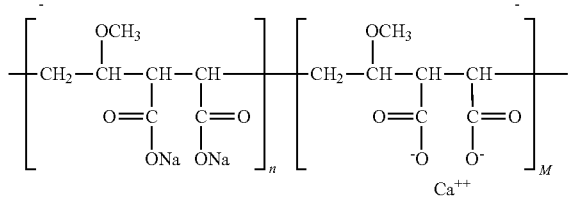

where m is an integer that provides molecular weight for the polymer between about 60,000 and about 500,000.

Preferred are 1:4 to 4:1 copolymers of maleic anhydride or acid with another polymerizable ethylenically unsaturated monomer, preferably methyl vinyl ether (maleic anhydride) having a molecular weight of about 30,000 to about 1,000,000.

Sodium and calcium salts of carboxymethyl cellulose ether polymers can also be used including sodium and calcium salts of carboxymethyl cellulose ether, hydroxyethyl cellulose ether, sodium cellulose ether, etc.

Figure 5:
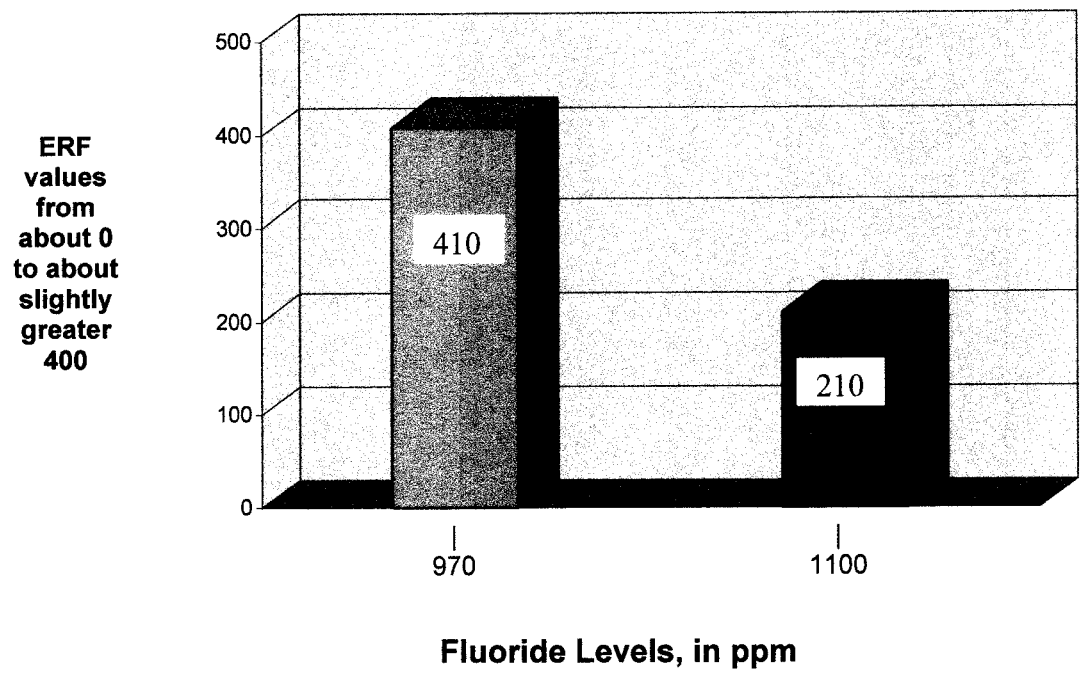
Figure 6:
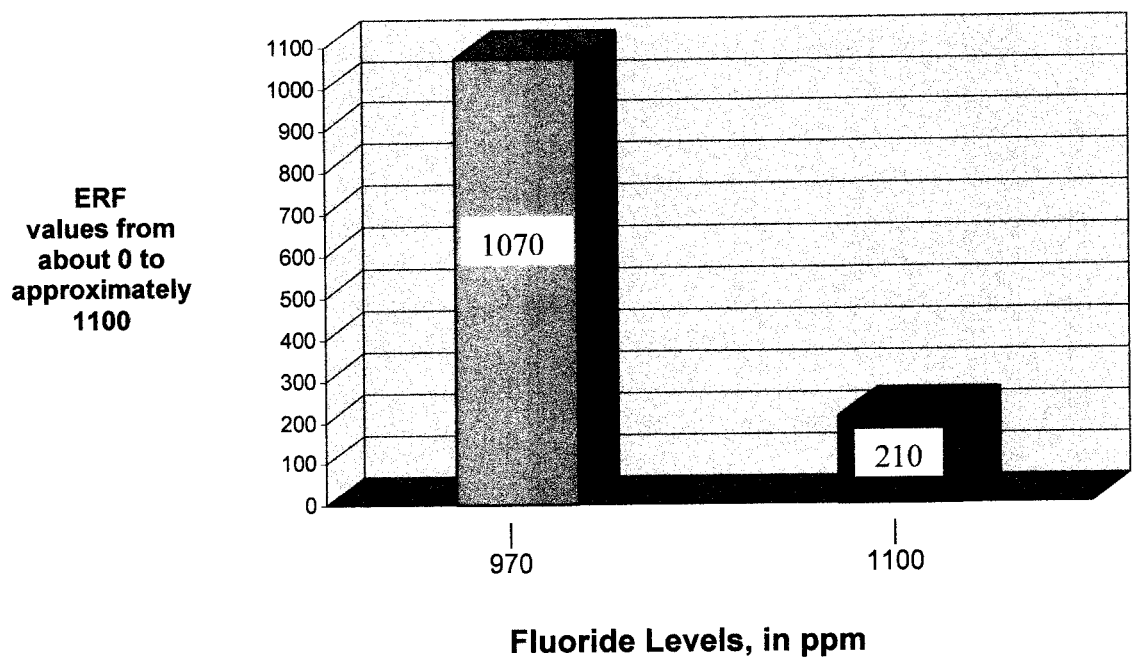

The contribution of $Ca^{++}$ from the copolymer substantivity enhancer to ERF values is illustrated in FIGS. 5 and 6 of the Drawings and Tables 6 and 7.

EXAMPLES 1 Through 5

The following stannous fluoride brushing gel samples were prepared, as described below, and subsequently tested for EPF and/or ERF values, as described in Tables 2 through 8 below:

EXAMPLES 1 and 2

EXAMPLE 1

In a stainless steel 1 L mixing vessel, using an overhead stirrer, 26.966 gm of PEG 400 were added along with 82.768 gm of glycerin, and 48.78 gm of 1.64% stannous fluoride in glycerin. Stirring was begun at a low speed while heating to 80° C. Then 2.84 gm of L-1220/2.5 million cs (10%) ULTRAMULSION® substantivity agent was added with stirring for 15 minutes. The overhead stirrer speed was increased to medium and 1.88 gm of Gantrez MS-955 substantivity enhancer was added with stirring for 5 minutes. Then Crodasinic L, 1.42 gm; Sucralose, 0.18 gm; and insoluble saccharin, 0.56 gm were added with continued stirring for 10 minutes. TEGO betaine CKD, 1.42 gm, was added and stirred for 5 minutes. Calcium fumarate, anhydrous, micronized, 2.84 gm, was added with stirring for 5 minutes followed by addition of sodium dihydogen phosphate, anhydrous, micronized, 0.612 gm, was added with continued stirring for 5 minutes.

In multiple increments, Sipernat 22S, 28.3 gm was added with stirring 2 minutes between each addition. When the Sipernat 22S was all added, stirring continued for 15 minutes after which Vanillamint, 1.32 gm, and Multisensate flavor, 0.114 gm, were added with continued stirring for 5 minutes. The stirrer was removed and the gel was filled into dispensing tubes. When used as a brushing gel, a pleasant, refreshing mouthfeel and very little metallic taste is perceived.

EXAMPLE 2

Using the procedure described in Example 1, a second brushing gel was formulated without the Gantrez MS-955 substantivity enhancer.

EXAMPLES 3 Through 5

Figure 4:
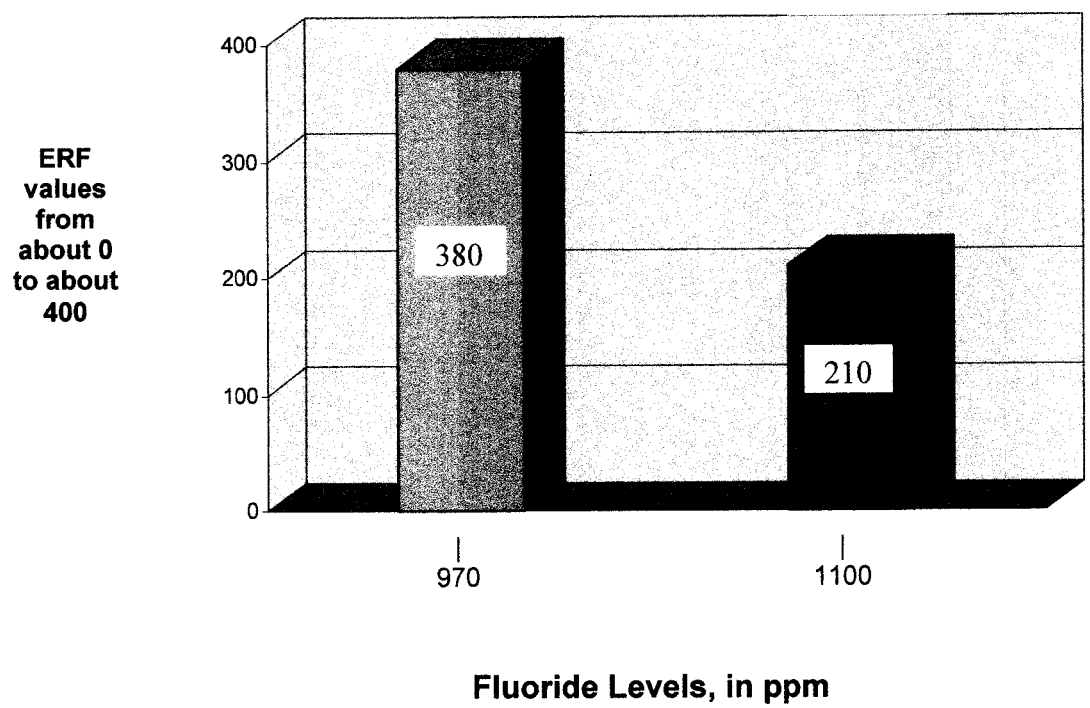
FIGS. 4 through 6 present ERF values for brushing gels of the present invention comprising compositions, as described in Examples 3 through 5. Specifically, in FIG. 4 the 380 ERF value is for a test gel, stannous fluoride at 970 ppm fluoride; and the 210 ERF value is for Crest® PRO-HEALTH®, stannous fluoride at 1100 ppm fluoride.

Three STANNOUS FLUORIDE BRUSHING GEL formulations, described below, were prepared using the method described above for Examples 1 and 2. These brushing gel formulations were in vitro tested. The results are reported in Tables 5 through 7 and in
FIGS. 4 through 6 of the Drawings.

EXAMPLE 3

Stannous Fluoride Brushing Gel

| Ingredients | Percent | Grams |
|---|---|---|
| PEG 400 | 13.653 | 68.265 |
| Glycerin | 41.384 | 206.92 |
| 1.64% Stannous Fluoride in Glycerin | 24.39 | 121.95 |
| L-1220/2.5 million CS ULTRAMULSION ® 10% (substantivity agent) | 1.42 | 7.1 |
| Multisensate (flavor enhancer) | 0.057 | 0.285 |
| Gantrez MS-955 (substantivity agent) | 0.94 | 4.7 |

-continued

| Ingredients | Percent | Grams |
|---|---|---|
| Vanillamint P | 0.66 | 3.3 |
| Insoluble Saccharin | 0.28 | 1.4 |
| Tego Betaine CKD | 0.71 | 3.55 |
| Sipernat 228 | 14.15 | 70.75 |
| Crodasinic L | 0.71 | 3.55 |
| Sucralose | 0.09 | 0.45 |
| Calcium Sulfate | 1.25 | 6.25 |
| Sodium Phosphate Monobasic Anhy. | 0.306 | 1.53 |
| Total | 100 | 100 |

EXAMPLE 4

Stannous Fluoride Brushing Gel

| Ingredients | Percent | Grams |
|---|---|---|
| PEG 400 | 13.483 | 67.415 |
| Glycerin | 41.384 | 206.92 |
| 1.64% Stannous Fluoride in Glycerin | 24.39 | 121.95 |
| 2.5 million CS ULTRAMULSION ® 10% (substantivity agent) | 1.42 | 7.1 |
| Multisensate (flavor enhancer) | 0.057 | 0.285 |
| Gantrez MS-955 (substantivity agent) | 0.94 | 4.7 |
| Vanillamint P | 0.66 | 3.3 |
| Insoluble Saccharin | 0.28 | 1.4 |
| Tego Betaine CKD | 0.71 | 3.55 |
| Sipernat 228 | 14.15 | 70.75 |
| Crodasinic L | 0.71 | 3.55 |
| Sucralose | 0.09 | 0.45 |
| Calcium Fumarate | 1.42 | 7.1 |
| Sodium Phosphate Monobasic Anhy. | 0.306 | 1.53 |
| Total | 100 | 100 |

EXAMPLE 5

Stannous Fluoride Brushing Gel

| Ingredients | Percent | Grams |
|---|---|---|
| PEG 400 | 15.149 | 75.745 |
| Glycerin | 42.384 | 211.92 |
| 1.64% Stannous Fluoride in Glycerin | 24.39 | 121.95 |
| L-1220/2.5 million CS ULTRAMULSION ® 10% (substantivity agent) | 1.42 | 7.1 |
| Multisensate (flavor enhancer) | 0.057 | 0.285 |
| Vanillamint P | 0.66 | 3.3 |
| Insoluble Saccharin | 0.28 | 1.4 |
| Tego Betaine CKD | 0.71 | 3.55 |
| Sipernat 228 | 14.15 | 70.75 |
| Crodasinic L | 0.71 | 3.55 |
| Sucralose | 0.09 | 0.45 |
| Total | 100 | 100 |

In Vitro Testing

In vitro determination of EPF values attributed to administration of various fluoride containing: toothpastes and a test brushing gel onto human enamel subjected to acid challenge.

The following study was carried out according to the FDA Monograph on Anticaries Drug Products for over-the-counter, human use. The study was performed following FDA good laboratory practices.

Purpose of the following in vitro study: to determine the effect of acid challenge to human enamel treated with various fluoride containing brushing products. The effect of the acid challenge was established by measuring the resistance of enamel specimens treated with various fluoride brushing products to an acid challenge; before and after treatment with various fluoride brushing products.

Tooth Preparation:

Three sound human molars were placed in a disc of red boxing wax so that only the enamel surfaces were exposed. Twelve set of three teeth each were prepared for the study. All specimens were cleaned and polished with a flour of pumice slurry and a rag wheel to remove any deposits or stains.

Preparation of Buffered Lactic Acid Challenge Solution:

Two moles (203.58 g of 88.5% pure lactic acid were diluted with approximately 500 ml of distilled water. To this was added a solution of 84 g NaOH dissolved in about 600 ml of distilled water. The total volume was then adjusted to 2000 ml. This was the buffered 1.0 M lactic acid challenge solution.

Another lactic acid solution was prepared by diluting two moles lactic acid to 2000 ml with distilled water. The solution of lactic acid and sodium hydroxide was placed in a 4000 ml beaker, and pH electrodes placed in the solution. The 1.0 M lactic acid solution was used to adjust the pH of the buffered solution to 4.5. To obtain a 0.1 working concentration (for all decalcifications) the 1.0 M buffer was diluted by a factor of 10 with distilled water.

Deprotection:

Before every use, any residual anti-solubility protection afforded by the previous treatment was eliminated. Deprotection of these specimens was accomplished by etching the teeth in the above prepared 0.1M lactate buffer solution for a two-hour period. Each disc of three specimens was agitated (450 rpm) in about 50 ml of lactate buffer at room temperature during the deprotection period. The teeth were rinsed well with distilled water immediately following deprotection.

Pre-Treatment Etch:

The test was performed using preheated (37° C.) tooth sets and lactate buffer. The deprotected tooth sets were mounted on ¼ inch diameter acrylic rods with molten red boxing wax. Multiplaced stirrers were used for treatments and the etches. All slurries and solutions were pre-heated to 37° C. The actual treatments and etches were carried out on the bench top with the preheated solutions. Plastic specimen containers (120 ml) were used for the etching procedure. A ¼ inch hole was drilled in each container lid to accommodate the plastic rod to which the tooth sets were mounted. A 40 ml portion of 0.1M lactic acid buffer was placed in each container along with a one-inch magnetic stirring bar. The rod of the first tooth set was pushed through the hole in the lid, placed in the first container and adjusted so that all enamel surfaces were immersed into the buffer solution. The container was then placed on the first magnetic stirrer and stirring was begun. The timer was started at this time. At 30-second intervals the other tooth sets were started in the same manner. After 15 minutes of exposure to the buffered lactate solution, the first set was stopped and the lid and tooth set immediately removed from the container and placed in a tray of distilled water to terminate etching. The other sets were similarly removed at 30 second intervals in the same order that they were initiated and the lactate buffer solutions was retained for phosphorus analysis. The tooth sets were placed back in the 37° C. water bath in preparation for the fluoride treatment step.

Treatment:

The treatments were performed using slurries of the fluoride brushing products. The slurries consisted of 1 part fluoride brushing product and 3 parts preheated (37° C.) distilled water (9 g:27 ml). Each slurry was mixed for exactly one minute after adding the water. The slurries were NOT prepared ahead of time. They were NOT centrifuged. All tooth sets were treated at the same time (one for each fluoride brushing product). The treatment procedure was similar to the etching procedure with the exception of the slurry in place of the acid. A 30 ml portion of the preheated fluoride brushing slurry was added to the first tooth set, the teeth were immersed in the slurry and the container placed on the first stirrer. The stirrer and timer were started. At 90-second intervals (to allow time for stirring), the other tooth sets were started in the same manner. At the end of the five minutes of treatment, the first set was stopped, the tooth set removed and rinsed well with distilled water. The other sets were removed at 90-second intervals and rinsed well. The treatment fluoride brushing slurries were discarded.

Post-Treatment:

A second acid exposure was then performed by the same method as the pre-treatment etch and the lactate buffer solutions were again retained for phosphorus analysis. The pre and post-treatment solutions were analyzed using a Klett-Summerson Photoelectric Colorimeter.

Repeat Analyses:

The tooth sets were deprotected and the procedure repeated additional times so that each fluoride brushing product was treated and assayed on each tooth set. The treatment design was a Latin Square design so that no treatment followed another treatment consistently.

Calculation of Enamel Solubility Reduction:

The percent of enamel solubility reduction was computed as the difference between the amount of phosphorus in the pre and post acidic solutions, divided by the amount of phosphorus in the pre solution and multiplied by 100.

Treatment Groups:

A. Placebo (deionized water)
B. Positive control 1 Crest® PRO-HEALTH® Toothpaste with stannous fluoride @ 1100 ppm fluoride
C. Positive control 2 ClinPro® 5000 Toothpaste with sodium fluoride at 5000 ppm fluoride
D. Test Gel with stannous fluoride at 970 ppm fluoride composition as described hereinafter in Example 1.

Statistical Analyses:

Statistical analyses of the individual means were performed with a one-way analysis of variance model using Sigma Stat (3.1) Software. Since the ANOVA indicated significant differences, the individual means were analyzed by the Student Newman-Keuls (SNK) test.

Results and Discussion:

The deionized water negative control was not effective in reducing enamel solubility. The positive fluoride containing controls and the test gel were significantly more effective than the deionized water negative control. The Clinpro 5000® toothpaste was significantly more effective than the negative control. The Test Gel was significantly more effective than the other two positive controls in reducing enamel solubility.

The results are shown in Table 2 below:

TABLE 2

ENAMEL SOLUBILITY REDUCTION
Summary of Results

| Group | Treatment | Pre-Etch μP | Post-Etch μP | Delta μP | Percent Reduction | EPF ** |
|---|---|---|---|---|---|---|
| A | Deionized Water | 583 ± 24* | 633 ± 22 | −50 ± 13 | −9.06 ± 2.28 | — |
| B | Crest ® PRO-HEALTH ® (stannous fluoride @ 1100) | 645 ± 23 | 488 ± 14 | 158 ± 18 | 23.83 ± 2.27 | 2.2 |
| C | Clinpro 5000 ® (sodium fluoride @ 5000 ppm) | 617 ± 21 | 582 ± 21 | 35 ± 14 | 5.49 ± 2.28 | 0.1 |
| D | Brushing Gel (stannous fluoride @ 970 ppm fluoride) used in a method of treatment of the present invention See Example 1 | 654 ± 39 | 409 ± 12 | 245 ± 32 | 35.79 ± 2.91 | 3.7 |

*Mean ± SEM (N = 12)
** To establish the enamel protection factor (EPF) values for each fluoride brushing product tested, the percent reduction in enamel solubility was divided by the fluoride level in parts per million of the brushing product tested. The resultant number was multiplied by 100.
See FIG. 1 of the Drawings.

In Vitro Determination of ERF Values Attributed to Administration of Various Fluoride Containing Toothpastes and a Brushing Gel of the Present Invention onto Incipient Enamel Lesions in Bovine Enamel.

The following study was carried out according to the FDA Monograph on Anticaries Drug Products for over-the-counter, human use, following FDA good laboratory practices.

Purpose of the following in vitro study: to determine the fluoride uptake into incipient enamel lesions in bovine incisors, treated with various fluoride containing, brushing products.

The test procedure was identical to the procedure identified as Procedure 40 in the FDA anticaries Monograph, except the lesions were formed using a solution comprising 0.1 M lactic acid and 0.2% Carbopol 907, wherein the solution was saturated with HAP (hydroxyapatite) at a pH of 5.0.

The fluoride uptake was established by analyzing fluoride and calcium levels of enamel pre-treatment and enamel post-treatment to determine the change in enamel fluoride attributed to treatment with fluoride containing brushing products.

Procedure:

Sound, upper, central, bovine incisors were selected and cleaned of all adhering soft tissue. A core of enamel 3 mm in diameter was prepared from each tooth by cutting perpendicularly to the labial surface with a hollow-core diamond drill bit. This was performed under water to prevent overheating of the specimens. Each specimen was embedded in the end of a plexiglass rod (¼" diameter×2" long) using methylmethacrylate. The excess acrylic was cut away exposing the enamel surface. The enamel specimens were polished with 600 grit wet/dry paper and then micro-fine Gamma Alumina. The resulting specimens were a 3 mm disk of enamel with all but the exposed surface covered with acrylic. Twelve specimens per group were prepared.

Each enamel specimen was then etched by immersion into 0.5 ml of 1M $HClO_4$ for 15 seconds. Throughout the etch period, the etch solutions were continuously agitated. A sample of each solution was then buffered with TISAB (fluoride ion probe buffer) to a pH of 5.2 (0.25 ml sample, 0.5 ml TISAB and 0.25 ml 1N NaOH) and the fluoride content of the solution determined by comparison to a similarly prepared standard curve (1 ml std+1 ml TISAB). For use in depth of each calculation, the Ca content of the etch solution was determined by taking 50 μl and analyzing for Ca by atomic absorption (0.05 ml qs to 5 ml). These data was the indigenous fluoride level of each specimen prior to treatment.

The specimens were once again ground and polished as described above. An incipient lesion was formed in each enamel specimen by immersion into a 0.1M lactic acid/0.2% Carbopol 907 solution for 24 hours at room temperature. These specimens were then rinsed well with distilled water and stored in a humid environment until used.

The treatments were performed using slurries of the various fluoride containing brushing products. The flurries consisted of 1 part fluoride containing brushing product and 3 parts distilled water (9 g:27 ml). Each slurry was mixed for exactly one minute after adding the water. The slurries were NOT prepared ahead of time. They were NOT centrifuged. The 12 specimens of each group were then immersed into 25 ml of their assigned slurry with constant stirring (350 rpm) for 30 minutes. Following treatment, the specimens were rinsed with distilled water. One layer of enamel was then removed from each specimen and analyzed for fluoride and calcium as outlined above (i.e. 15 second etch). The pretreatment fluoride (indigenous) level of each specimen was then subtracted from post treatment, fluoride value to determine the change in enamel fluoride due to the last treatment.

Statistical Analyses:

All raw data (individual specimen Enamel Fluoride Uptake (EFU) values wee reported. In addition, the mean, S.D. (standard deviation) and SEM (scanning electron micrograph) for each group was calculated. Statistical analysis were performed by a one-way analysis of variance model using Sigma Stat Software (3.1). Since significant differences are indicated, the individual means were analyzed by the Student Newman Keuls (SNK) test.

Test Products:

The test fluoride containing brushing products were coded as follows:

1. Placebo (deionized water)
2. Positive Control 1 Crest® PRO-HEALTH® with stannous fluoride at 1100 ppm fluoride
3. Positive control 2 Clinpro 5000® with sodium fluoride at 5000 ppm fluoride
4. Brushing Gel of the present invention with stannous fluoride at 970 ppm fluoride composition as described in Example 1.

Results:

The results are shown in Table 3 below:

TABLE 3

Change in Incipient Lesion Enamel Fluoride Content

| Fluoride Containing Brushing Product | Enamel Fluoride Concentration (ppm) | | | | |
|---|---|---|---|---|---|
| | Pre Treatment | Post Treatment | Increase | Etch Depth | ERF*** |
| Placebo, deionized water | 41 ± 4* | 44 ± 3 | 3 ± 2 | 17.88 ± 0.70 | — |
| Crest ® PRO-HEALTH ® @ 1100 stannous fluoride | 44 ± 5 | 1888 ± 81 | 1843 ± 83 | 10.06 ± 0.25 | 170 |
| Clinpro 5000 ® @ 5000 ppm sodium fluoride | 52 ± 6 | 3310 ± 88 | 3258 ± 88 | 15.28 ± 0.56** | 65 |
| Brushing Gel @ 970 ppm stannous fluoride See Example 1 | 47 ± 5 | 3003 ± 212 | 2956 ± 212 | 13.36 ± 0.26 | 300 |

*Mean ± SEM (N = 12)

**Values 15.32 and 15.28 are not significantly different

***To establish the enamel repair factor (ERF) values for each fluoride brushing product tested, the increase in enamel fluoride concentration was divided by the fluoride level of the fluoride brushing product. The resultant number was multiplied by 100.

Figure 2:
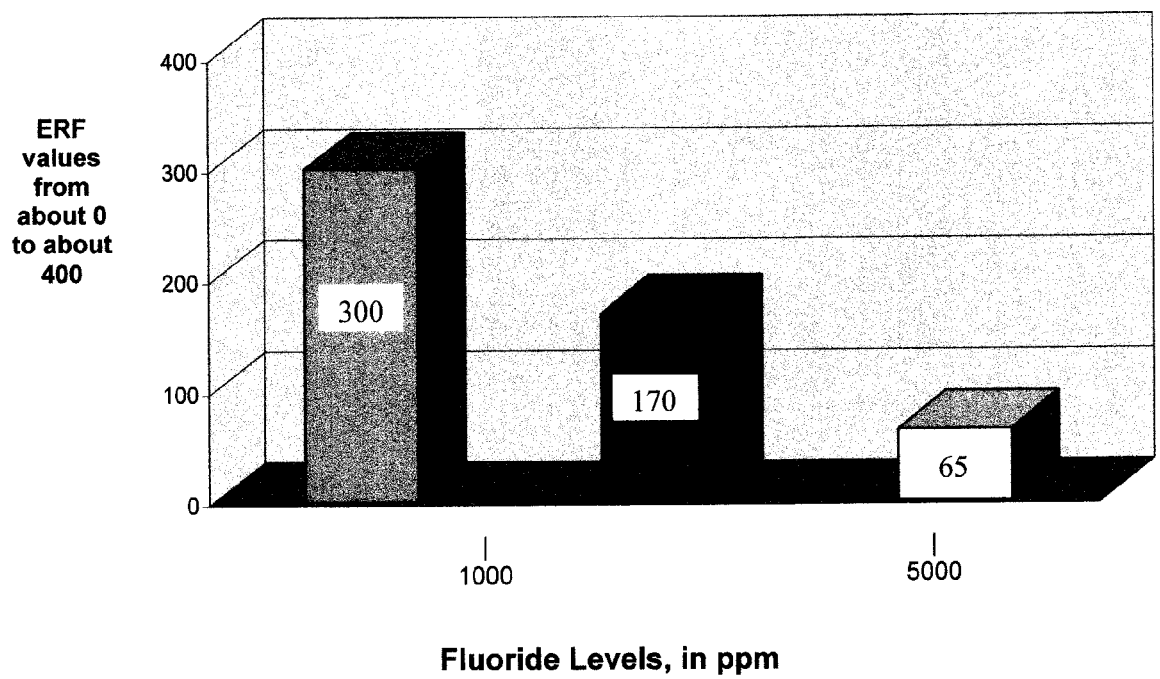
FIGS. 2 and 3 of the Drawings illustrate enamel repair factor (ERF) values for brushing gels of the present invention with compositions, as described in Examples 1 and 2; with stannous fluoride at 970 ppm compared with toothpastes having stannous fluoride at 1100 ppm and sodium fluoride at 900 ppm or sodium fluoride at 5000 ppm, respectively.

See FIG. 2 of the Drawings.

In vitro determination of ERF values attributed to administration of various fluoride containing: toothpastes and a brushing gel of the present invention onto incipient enamel lesions in human enamel was carried out following the Enamel Fluoride protocol described above for the results reported in Table 3. Some of the fluoride containing brushing products tested in this fluoride uptake study are different than those reported on in Table 3 above.

TABLE 4

Change in Incipient Lesion Enamel Fluoride Content

| Fluoride Containing Brushing Product | Enamel Fluoride Concentration (ppm) | | | | |
|---|---|---|---|---|---|
| | Pre Treatment | Post Treatment | Increase | Etch Depth | ERF** |
| Placebo, deionized water | 41 ± 4* | 89 ± 5 | 47 ± 5 | 17.88 ± 0.70 | — |
| Crest ® PRO-HEALTH ® Toothpaste (stannous fluoride, 1100 ppm fluoride) | 44 ± 5 | 1530 ± 69 | 1486 ± 66 | 10.06 ± 0.25 | 140 |
| Brushing Gel (stannous fluoride at 970 ppm fluoride) See Example 2 | 52 ± 6 | 2656 ± 80 | 2615 ± 79 | 15.26 ± 0.56 | 270 |

Figure 3:
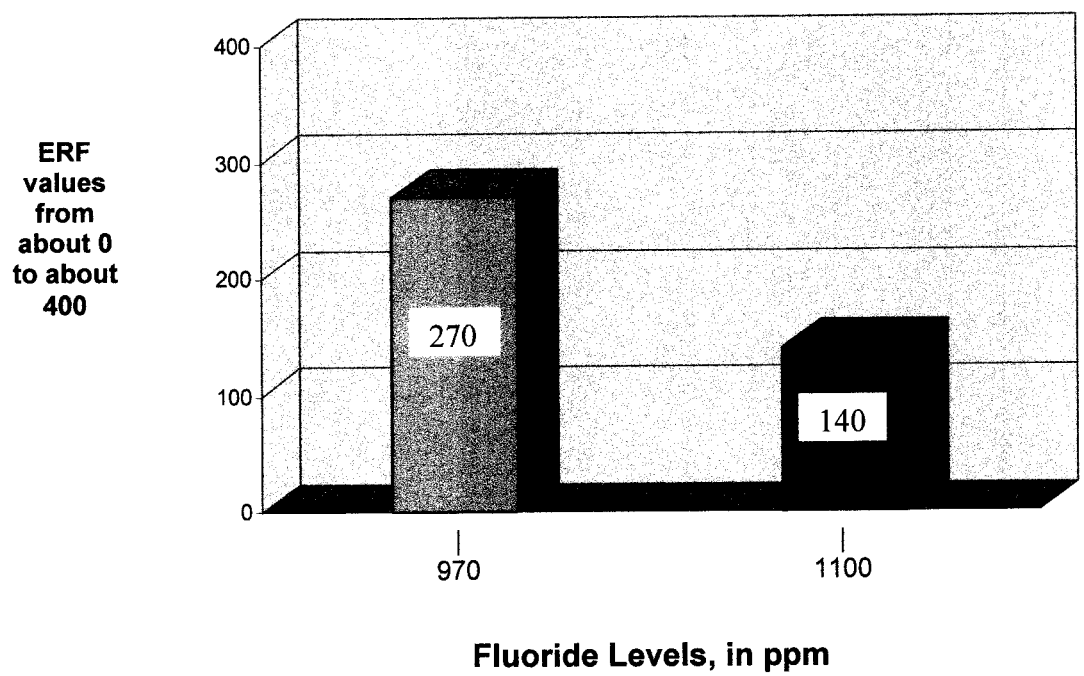

*Mean ± SEM (N = 12)
**To establish the enamel repair factor (ERF) values for each fluoride brushing product tested, the average increase in enamel fluoride concentration (post treatment was divided by the fluoride level of the fluoride brushing product tested. The resultant number was multiplied by 100).
See FIG. 3 of the Drawings

TABLE 5

Change in Incipient Lesion Enamel Fluoride Content

| Fluoride Containing Brushing Product | Enamel Fluoride Concentration (ppm) | | | | |
|---|---|---|---|---|---|
| | Pre Treatment | Post Treatment | Increase | Etch Depth | ERF** |
| Placebo, deionized water | 46 ± 4* | 56 ± 4 | 9 ± 4 | 17.55 ± 0.28 | — |
| Crest ® PRO-HEALTH ® Toothpaste (stannous fluoride, 1100 ppm fluoride) | 57 ± 6 | 2338 ± 73 | 2280 ± 76 | 9.51 ± 0.35 | 210 |
| Brushing Gel (stannous fluoride at 970 ppm fluoride) See Example 5 | 48 ± 5 | 3034 ± 117 | 2987 ± 114 | 11.15 ± 0.18 | 380 |

*Mean ± SEM (N = 12)
**To establish the enamel repair factor (ERF) values for each fluoride brushing product tested, the average increase in enamel fluoride concentration (post treatment was divided by the fluoride level of the fluoride brushing product tested. The resultant number was multiplied by 100).
See FIG. 4 of the Drawings.

TABLE 6

Change in Incipient Lesion Enamel Fluoride Content

| Fluoride Containing Brushing Product | Enamel Fluoride Concentration (ppm) | | | | |
|---|---|---|---|---|---|
| | Pre Treatment | Post Treatment | Increase | Etch Depth | ERF** |
| Placebo, deionized water | 46 ± 4* | 56 ± 4 | 9 ± 4 | 17.55 ± 0.28 | — |
| Crest ® PRO-HEALTH ® Toothpaste (stannous fluoride, 1100 ppm fluoride) | 57 ± 6 | 2338 ± 73 | 2280 ± 76 | 9.51 ± 0.35 | 210 |
| Brushing Gel (stannous fluoride at 970 ppm fluoride) See Example 3 | 56 ± 4 | 4032 ± 216 | 3976 ± 217 | 10.84 ± 0.24 | 410 |

*Mean ± SEM (N = 12)
**To establish the enamel repair factor (ERF) values for each fluoride brushing product tested, the average increase in enamel fluoride concentration (post treatment was divided by the fluoride level of the fluoride brushing product tested. The resultant number was multiplied by 100).
See FIG. 5 of the Drawings.

TABLE 7

Change in Incipient Lesion Enamel Fluoride Content

| Fluoride Containing Brushing Product | Enamel Fluoride Concentration (ppm) | | | | |
|---|---|---|---|---|---|
| | Pre Treatment | Post Treatment | Increase | Etch Depth | ERF** |
| Placebo, deionized water | 46 ± 4* | 56 ± 4 | 9 ± 4 | 17.55 ± 0.28 | — |
| Crest ® PRO-HEALTH ® Toothpaste (stannous fluoride, 1100 ppm fluoride) | 57 ± 6 | 2338 ± 73 | 2280 ± 76 | 9.51 ± 0.35 | 210 |
| Brushing Gel (stannous fluoride at 970 ppm fluoride) See Example 4 | 57 ± 5 | 10462 ± 357 | 10406 ± 363 | 13.95 ± 0.39 | 1070 |

*Mean ± SEM (N = 12)
**To establish the enamel repair factor (ERF) values for each fluoride brushing product tested, the average increase in enamel fluoride concentration (post treatment was divided by the fluoride level of the fluoride brushing product tested. The resultant number was multiplied by 100).
See FIG. 6 of the Drawings.

TABLE 8

Summary of Stannous Fluoride Brushing Gel
ERF data, based on using methods of the present invention with various brushing gel compositions,
as described in Tables 3 through 7 and in FIGS. 2 through 6 of the Drawings

| Stannous Fluoride Brushing Gel described in: Table No/FIG. No. | Substantivity Agent (% by wt.) | $SnF_2$ in PPM F | Calcium Content % | Phosphate Content % | Fluoride Uptake | Substantivity Enhancer (% by wt) | Additional $Ca^{++}$ % | Total $Ca^{++}$ % | pH upon application to enamel | ERF |
|---|---|---|---|---|---|---|---|---|---|---|
| 3/2 (Example 1) | L-1220 & PDMS 2.5 million cs (1.42) | 970 | 0.369 | 0.242 | 2956 | 0.94 | 0.1 | 0.469 | 4.0 | 300 |
| 4/3 (Example 2) | L-1220 & PDMS 2.5 million cs (1.42) | 970 | 0 | 0 | 2615 | 0 | 0 | 0 | — | 270 |
| 5/4 (Example 5) | L-1220/2.5 million cs ULTRAMULSION ® 10% (1.42) | 970 | 0 | 0 | 2987 | — | 0 | 0 | — | 380 |
| 6/5 (Example 3) | L-1220/2.5 million cs ULTRAMULSION ® 10% (1.42) | 970 | 1.25 | 0.306 | 3976 | 0.94 | 0.1 | 1.35 | — | 410 |
| 7/6 (Example 4) | 2.5 million cs ULTRAMULSION ® 10% (1.42) | 970 | 1.42 | 0.306 | 10406 | 0.94 | 0.1 | 1.52 | — | 1070 |

TABLE 9

Illustrative Examples of Brushing Gels

| Example No. | Stannous Fluoride level in ppm fluoride | Poloxamer (% by wt.) | PDMS (% by wt.) | Substantivity Enhancer (% by wt.) | pH of GEL in saliva |
|---|---|---|---|---|---|
| 6 | 970 | L-1220 (1.8) | 2.5 million cs (0.2) | MS-955 (1.1) | 3.5 |
| 7 | 1100 | F-127 (2.7) | 800,000 cs (0.3) | MS-955 (0.94) | 3.0 |
| 8 | 600 | L-1220 (2.25) | 1.5 million cs (0.25) | MS-955 (0.97) | 5.6 |
| 9 | 800 | L-1220 (1.8) | 1.2 million (0.2) | MS-955 (0.94) | 4.5 |
| 10 | 500 | F-127 (2.25) | 1 million cs (0.25) | MS-955 (1.0) | 5.0 |
| 11 | 400 | F-127/L-1220 (0.8) | 2.5 million cs (0.2) | MS-955 (0.94) | 5.8 |

TABLE 9-continued

Illustrative Examples of Brushing Gels

| Example No. | Stannous Fluoride level in ppm fluoride | Poloxamer (% by wt.) | PDMS (% by wt.) | Substantivity Enhancer (% by wt.) | pH of GEL in saliva |
|---|---|---|---|---|---|
| 12 | 1000 | F-127/L-1220 (2.85) | 2 million cs (0.71) | MS-955 (1.16) | 3.7 |
| 13 | 700 | L-1220 (2.5) | 1.8 million cs (0.63) | MS-955 (1.0) | 4.8 |
| 14 | 850 | F-127 (2.1) | 2.5 million cs (0.23) | MS-955 (0.94) | 4.3 |

TABLE 10

Treatment of "at-risk" patients with Brushing GELS of the Invention

| "At-risk" Patient | Specific Brushing GEL Formulation Recommended | Frequency of Treatment | Duration of Treatment |
|---|---|---|---|
| Children under 7 years of age | Example 4 | Once daily for 2 minutes followed by expectorating | To be determined by pediatric dentist |
| Undergoing medical and/or professional oral care treatments with prescribed medications | Example 4 | At least twice daily | Duration of medical/professional oral care treatment |
| Immunocompromised with chronic conditions | Example 5 | At least twice daily | For term of chronic condition |
| Diabetes, heart disease, etc. | Example 3 | Several times daily | For term of chronic condition |
| Cancer treatment | Example 4 | As required | To be determined by oral care professional |

EXAMPLE 15

A 5 liter Ross/Olsa vacuum mixer with internal homogenizer was heated to 80 degrees C. while the vessel was charged with 647.15 gm of PEG 400, 2069.2 gm of anhydrous glycerin and 1219.5 gm of 1.64% stannous fluoride/glycerin. Anchor stirring at slow speed was begun and continued for 7 minutes. ULTRAMULSION® [(Plurocare L-1220 (90%)) and 2.5 million cs polydimethylsiloxane (10%), 71 gm, was added with homogenizer speed adjusted to 2500 rpm for 15 minutes. The anchor stirrer was increased to medium speed and Gantrez MS-955, 47 gm, was added with stirring and homogenizing for 5 minutes. Crodasinic L, 35.5 gm, was added with continued stirring for 5 minutes. TEGO Betaine CKD, 35.5 gm, was added and stirring continued for 5 minutes. Micronized (20 micron D50) calcium fumarate, anhydrous, 71 gm, was added with stirring for 5 minutes. Micronized (20 micron) sodium phosphate monobasic, anhydrous, 15.3 gm, was added with stirring for 5 minutes. Sident 22S, 707.5 gm, was added in increments at 2 minutes between additions until all was added. Stirring was continued for 15 minutes.

Vanillamint P flavor, 33 gm, and spilanthes extract, 2.85 gm, were added with continued stirring for 5 minutes. The vessel was cooled to ambient temperature over 15 minutes. The contents were dispensed into tubes for use. Upon dispensing, the brushing gel was pleasant testing with no stannous fluoride aftertaste. Stannous fluoride stability testing was performed on the product.

Discussion of EPF and ERF Values Established by In Vitro Testing

The stannous fluoride brushing gels of the present invention show substantial improvement in EPF and ERF values compared to commercial toothpastes at various fluoride levels as reported in: Tables 2 through 7, FIGS. 1 through 6 of the Drawings and Summary Table 8.

For example, the ERF values, reported in Table 3 and FIG. 2 for a Crest® PRO-HEALTH® and Clinpro 5000® toothpastes are 170 and 65 respectively, compared to an ERF for the stannous fluoride brushing gel of the present invention of 300. The ERF values reported in Table 7 and FIG. 6 of the Drawings for Crest® PRO-HEALTH® toothpaste is 210 compared to an ERF for the Stannous Fluoride Brushing Gel of the present invention, 1070.

These 2× and 5× improvements, respectively, in ERF value over commercial toothpastes represent a major advance in fluoride uptake and enamel hardening. Such an advantage in enamel hardening efficiency is particularly critical to children as well as to patients experiencing: rampant caries, coronal caries, cancer therapy treatments, mucositis treatments, immune deficiency treatments, bone marrow transplants, etc.

Proposed Mechanism of Action of the Compositions of the Present Invention

The enamel protectant and/or enamel repair (EPF and/or ERF) data reported for formulations described in Examples 1 through 5, as detailed in Tables 2 through 8 and in FIGS. 1 through 6 of the Drawings, suggest the substantivity of stannous fluoride and calcium to the biofilm present on enamel surfaces is enhanced by a shift from bidentate to monodentate calcium binding in the presence of stannous fluoride. This shift in calcium binding in the presence of stannous fluoride results in a most effective binding site configuration. See:

Dudey and Lim, *J. Phys. Chem B*, 2004, 108:4546.
Vogel, et. al., *Caries Res.*, 2010, 94:108-115.
Rolla and Bowen, *Scand. J. Dent. Res.*, 1977; 85:149-151.
Rose, et. al., *J. Dent. Res.*, 1993; 72:78-84.
See also:
Turner, et. al., *Ceramics*, Silikaty 57(1):1-6 (2013)
Mohammed, et. al., *Caries Res.*, 47:421-428 (2013)

Calcium-Bridge, Fluoride Binding

Calcium binding to biofilm shifts from a bidentate chelation to a monodentate chelation in the presence of fluoride, freeing up calcium to bind with fluoride, $CaF^+$ pair, thereby doubling the calcium binding capacity.

Stable fluoride in the brushing gels of the present invention produces marked reduction in calcium binding affinity and approximately doubles calcium binding capacity. In the absence of fluoride, calcium binding to biofilm is bidentate. Stable fluoride in the brushing gels of the present invention compete with biofilm causing calcium binding to biofilm to become monodentate. This allows the binding of about double the quantity of calcium and of $CaF^+$ bound to biofilm. Release of fluoride bound by calcium bridging into biofilm fluid as a result of fluoride clearance into saliva will always be accompanied by a corresponding release of calcium which, in turn, potentiates the cariostatic effect of fluoride as indicated in the in vitro testing described in Tables 2 through 7 and FIGS. 1 through 6 of the Drawings.

At least some of the stable fluoride present in the brushing gels of the present invention is bound to calcium ions (sourced from various calcium salts in the present invention and/or calcium present in the copolymer substantivity enhancer, such as Gantrez® MS-955). These calcium ions, in turn, are bound to biofilm associated with enamel.

A drop in pH follows exposure of plaque to sucrose which removes some anionic groups by neutralization, thereby liberating calcium and fluoride (as $CaF^+$) at the very sites where these moieties can do the most good.

The effectiveness of the Brushing Gel compositions of the present invention depends on three factors:

(1) substantivity of the formulation to biofilm,
(2) stannous fluoride as the source of $CaF^+$, and
(3) retention of fluoride in a form on biofilm which allows release of $CaF^+$ ions into hydroxyapatite.

Stannous fluoride produces a marked reduction in calcium binding affinity accompanied by an approximate doubling of the calcium binding capacity. In the absence of fluoride, divalent cation binding to plaque is bidentate. Fluoride competes with macromolecular anionic groups, causing binding to become monodentate. Release of fluoride formed by calcium bridging, is accompanied by release of calcium, which potentiates the cariostatic effect of fluoride.

The presence $CaF^+$ is required to deliver the enamel protection and repair (EPF and ERF) results required for the Brushing Gel formulations of the present invention.

Summary as to the Role of Cation Bridging in Microbial Fluoride Binding

Fluoride binding produces a marked reduction in calcium binding affinity, along with a doubling of calcium binding capacity. This indicates that calcium binding changes from bidentate to monodentate. This shift from bidentate to monodentate is a consequence of fluoride replacing an anionic group as one of the calcium ligends.

The anionic groups to which calcium is no longer bound are then free to bind a $CaF^+$ ion pair, resulting in a doubling of the calcium binding capacity. Release of fluoride, bound by calcium bridging into plaque fluid, may be accompanied by a release of calcium which will potentiate the cariostatic effect of fluoride.

$CaF^+$ is taken up by hydroxyapatite and is responsible for the EPF and ERF in vitro data reported for the compositions of the present invention. The ERF values reported in Tables 3 through 8 and FIGS. 2 through 6 of the Drawings suggest that the $CaF^+$ moiety is incorporated into the hydroxyapatite lattice during remineralization.

The brushing gels of the present invention set a new, oral care standard for Enamel Protection and Enamel Repair, while dramatically reducing exposure to elevated fluoride levels in various fluoride varnishes, gels and toothpastes.

What is claimed is:

1. An aqueous-free, enamel protectant and enamel repair, brushing gels containing: stannous fluoride and calcium in a substantivity agent selected from solid and liquid, nonionic poloxamers and combinations thereof, wherein:

(a) Substantivity of said stannous fluoride and calcium into biofilm present on enamel is enhanced through a shift in calcium binding from bidentate to monodentate in the presence of stannous fluoride;

(b) EPF and ERF values of at least 2.5 and 200, respectively, are achieved with periodic administration of said brushing gels onto enamel surfaces with biofilm present;

(c) wherein the stannous fluoride is present in an amount of 400-1100 ppm;

(d) wherein the composition has a pH of 3-5.8;

(e) wherein the calcium content is 0.5-5.0%; and (f) wherein the calcium is limited to one or more of calcium fumarate, calcium sulfate, calcium gluconate, and mixed sodium and calcium salts of methyl/vinyl/ether/maleic copolymers thereof.

2. A composition according to claim 1, wherein some of said stannous fluoride and calcium is present as $CaF^+$.

3. A composition according to Claim 1, wherein said substantivity agent contains linear, polymeric polycarboxylate, substantivity enhancers.

4. Substantially aqueous-free, enamel protectant and enamel repair, brushing gels according to claim 3, containing stannous fluoride and calcium in a substantivity agent comprising an emulsion of polydimethylsiloxane polymer at viscosities from between about 10,000 cs and about 2.5 million cs as the discontinuous phase in a nonionic, liquid surfactant, continuous phase.

5. Brushing gels, according to claim 4, wherein nonionic liquid poloxamer surfactants, suitable for said brushing gels, are represented by the structural formula:

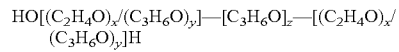

wherein the sum of x, y and z is from between 125 and 175.

6. Brushing gels, according to claim 3, wherein nonionic liquid surfactants, suitable for said brushing gels, are represented by the structural formula:

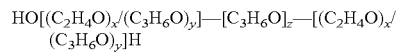

wherein x=76, y=25 and z=56.

7. Brushing gels, according claim 1, containing unreacted, calcium and phosphate components.

8. An aqueous-free, enamel protectant and enamel repair, brushing gels containing stannous fluoride and calcium in a substantivity agent comprising an emulsion of polydimethylsiloxane polymer at viscosities from between about 10,000 cs and about 2.5 million cs as the discontinuous phase in a nonionic, solid and liquid poloxamer surfactant, continuous phase and a linear polymeric polycarboxylates substantivity enhancer, wherein said nonionic surfactant is a liquid surfactant selected from the group consisting of solid and liquid surfactants having the following, general, structural formula:

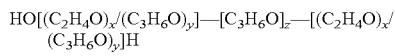
$HO[(C_2H_4O)_x/(C_3H_6O)_y]—[C_3H_6O]_z—[(C_2H_4O)_x/(C_3H_6O)_y]H$ wherein the sum of x, y and z is from between 125 and 175, wherein
  (a) Substantivity of said stannous fluoride and calcium into biofilm present on enamel is enhanced through a shift in calcium binding from bidentate to monodentate in the presence of stannous fluoride;
  (b) EPF and ERF values of at least 2.5 and 200, respectively, are achieved with periodic administration of said brushing gels onto enamel surfaces with biofilm present;
  (c) wherein the stannous fluoride is present in an amount of 400-1100 ppm;
  (d) wherein the composition has a pH of 3-5.8;
  (e) wherein the calcium content is 0.5-5.0%; and
  (f) wherein the calcium is limited to one or more of calcium fumarate, calcium sulfate, calcium gluconate, and mixed sodium and calcium salts of methyl/vinyl/ether/maleic copolymers thereof.

9. Brushing gels, according to claim 8, wherein nonionic, solid, poloxamer surfactants, suitable for said brushing gels, are represented by the structural formula:

$HO[(C2H4O)x/(C3H6O)y]-[C3H6Oz]-[(C2H4O)x/(C3H6O)y]H$ wherein the sum of x, y and z is from between 125 and 150.

10. Brushing gels, according to claim 8, wherein nonionic, solid, poloxamer surfactants, suitable for said brushing gels, are represented by the structural formula:

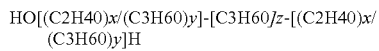
$HO[(C_2H_4O)_x/(C_3H_6O)_y]—[C_3H_6O]_z—[(C_2H_4O)_x/(C_3H_6O)_y]H$ wherein x =76, y=0 and z =56.

11. Brushing gels, according claim 8, containing unreacted, calcium and phosphate components.

12. An aqueous-free, enamel protectant and enamel repair, brushing gels, featuring monodentate-bidentate bonding of calcium in the presence of stannous fluoride; containing: stannous fluoride, calcium and phosphate components, and a substantivity agent emulsion containing liquid, nonionic, poloxamer surfactant as the continuous phase and polydimethylsiloxane polymer as the discontinuous phase; with an EPF of at least 2.5 and ERF of at least 200; wherein said nonionic surfactant is a liquid surfactant selected from the group consisting of liquid surfactants having the following, general, structural formula:

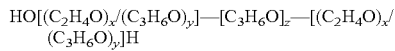
$HO[(C2H4O)x/(C3H6O),]-[C3H6O1z-[(C2H4O)x/(C3H6O)p1H$ wherein the sum of x, y and z is from between 125 and 175, wherein
  (a) Substantivity of said stannous fluoride and calcium into biofilm present on enamel is enhanced through a shift in calcium binding from bidentate to monodentate in the presence of stannous fluoride;
  (b) wherein the stannous fluoride is present in an amount of 400-1100 ppm;
  (c) wherein the composition has a pH of 3-5.8;
  (d) wherein the calcium content is 0.5-5.0%; and
  (e) wherein the calcium is limited to one or more of calcium fumarate, calcium sulfate, calcium gluconate, and mixed sodium and calcium salts of methyl/vinyl/ether/maleic copolymers thereof.

13. Brushing gels, according to claim 5, wherein said polydimethylsiloxane polymer discontinuous phase comprises up to 40% of said emulsion.

14. An aqueous-free, enamel protectant and enamel repair, brushing gels containing stable stannous fluoride and calcium on a substantivity agent selected from solid and liquid, nonionic poloxamers and combinations thereof substantive to biofilm coated enamel, wherein:
  (a) substantivity of said stannous fluoride and calcium into said biofilm is enhanced by a substantivity enhancer and by a shift from bidentate binding of calcium to monodentate in the presence of stable stannous fluoride;
  (b) said stannous fluoride, upon release from said substantivity agent, converts to the moiety CaFP which effects EPF and ERF values of at least 2.5 and at least 200, respectively, wherein said nonionic poloxamers is a liquid surfactant selected from the group consisting of liquid surfactants having the following, general, structural formula:

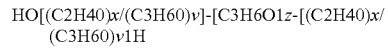
$HO[(C2H4O)x/(C3H6O)v]-[C3H6O1z-[(C2H4O)x/(C3H6O)v1H$ wherein the sum of x, y and z is from between 125 and 175;
  (c) wherein the stannous fluoride is present in an amount of 400-1100 ppm;
  (d) wherein the composition has a pH of 3-5.8;
  (e) wherein the calcium content is 0.5-5.0%; and
  (f) wherein the calcium is limited to one or more of calcium fumarate, calcium sulfate, calcium gluconate, and mixed sodium and calcium salts of methyl/vinyl/ether/maleic copolymers thereof.

15. Brushing gels according to claim 1, wherein said stannous fluoride, upon release from said substantivity agent, includes a CaF+ moiety in the presence of said calcium monodentate binding to said biofilm present on enamel.

16. Brushing gels according to claim 1, wherein the pH of said brushing gel, upon administration to enamel with biofilm, is about 3.

17. Brushing gels according to claim 3, wherein the level of said substantivity agent and said substantivity enhancers is between about 0.5 and about 5% by wt. and about 0.1 and about 3% by wt., respectively.

18. Brushing gels according to claim 3, wherein said substantivity enhancer has the structural formula:

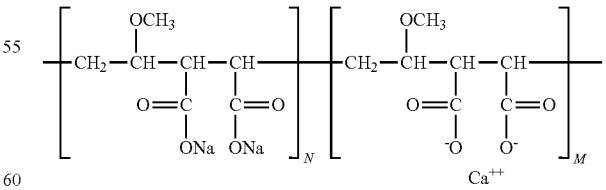

where m is an integer that provides weight between about 60,000 and about 1,000,000.

* * * * *